US011723876B2

(12) United States Patent
Park et al.

(10) Patent No.: US 11,723,876 B2
(45) Date of Patent: *Aug. 15, 2023

(54) BIODEGRADABLE POLYMER FORMULATIONS FOR EXTENDED EFFICACY OF BOTULINUM TOXIN

(71) Applicant: SK JOINT VENTURES II, LLC, New York, NY (US)

(72) Inventors: Kinam Park, West Lafayette, IN (US); Yeonhee Yun, West Lafayette, IN (US); Sarah Michelle Skidmore, Lafayette, IN (US); Byung Kook Lee, West Lafayette, IN (US); John Solomon Garner, West Lafayette, IN (US)

(73) Assignee: SK JOINT VENTURES II, LLC, New York, NY (US)

( * ) Notice: Subject to any disclaimer, the term of this patent is extended or adjusted under 35 U.S.C. 154(b) by 346 days.

This patent is subject to a terminal disclaimer.

(21) Appl. No.: 17/170,614

(22) Filed: Feb. 8, 2021

(65) Prior Publication Data

US 2021/0161826 A1 Jun. 3, 2021

Related U.S. Application Data

(63) Continuation of application No. 15/684,134, filed on Aug. 23, 2017, now Pat. No. 10,925,837.

(60) Provisional application No. 62/380,229, filed on Aug. 26, 2016.

(51) Int. Cl.
| | | |
|---|---|---|
| *A61K 9/50* | (2006.01) | |
| *A61K 47/36* | (2006.01) | |
| *A61K 47/34* | (2017.01) | |
| *A61K 9/00* | (2006.01) | |
| *A61K 9/16* | (2006.01) | |
| *A61K 9/14* | (2006.01) | |
| *A61K 9/51* | (2006.01) | |
| *A61K 38/48* | (2006.01) | |
| *C01G 9/04* | (2006.01) | |
| *C08G 63/08* | (2006.01) | |
| *A61K 9/113* | (2006.01) | |

(52) U.S. Cl.
CPC .......... *A61K 9/5031* (2013.01); *A61K 9/0024* (2013.01); *A61K 9/143* (2013.01); *A61K 9/146* (2013.01); *A61K 9/1647* (2013.01); *A61K 9/5153* (2013.01); *A61K 38/4893* (2013.01); *A61K 47/34* (2013.01); *A61K 47/36* (2013.01); *C01G 9/04* (2013.01); *C08G 63/08* (2013.01); *A61K 9/0019* (2013.01); *A61K 9/113* (2013.01)

(58) Field of Classification Search
CPC .... A61K 9/5031; A61K 9/0024; A61K 9/143; A61K 9/146; A61K 9/1647; A61K 9/5153; A61K 38/4893; A61K 47/34; A61K 47/36; A61K 9/0019; A61K 9/113; A61K 9/06; A61K 38/38; C01G 9/04; C08G 63/08

See application file for complete search history.

(56) References Cited

U.S. PATENT DOCUMENTS

| | | | | |
|---|---|---|---|---|
| 4,938,763 A | ‡ | 7/1990 | Dunn ...................... | A61L 27/50 604/89 |
| 6,306,423 B1 | ‡ | 10/2001 | Donovan ................ | A61P 21/00 424/42 |
| 6,312,708 B1 | * | 11/2001 | Donovan ................ | A61P 21/02 424/236.1 |
| 6,354,519 B1 | ‡ | 3/2002 | Kidooka ................. | A61B 1/126 239/46 |
| 6,383,509 B1 | ‡ | 3/2002 | Donovan ................ | A61P 25/14 424/42 |
| 6,506,399 B2 | ‡ | 1/2003 | Donovan ........... | A61K 38/4893 424/42 |
| 6,585,993 B2 | ‡ | 7/2003 | Donovan ............. | A61K 9/0024 424/42 |

(Continued)

FOREIGN PATENT DOCUMENTS

| | | | | |
|---|---|---|---|---|
| WO | | 9907343 | 2/1999 | |
| WO | | WO-9907343 A1 | ‡ 2/1999 | ........... A61K 9/0024 |

OTHER PUBLICATIONS

A. J. Stewart et al., "Interdomain zinc site on human albumin," PNAS, Apr. 1, 2003, vol. 11, No. 7, 3701-3706.‡

(Continued)

*Primary Examiner* — Monica A Shin
(74) *Attorney, Agent, or Firm* — Pabst Patent Group LLP

(57) ABSTRACT

Methods for the formulation of biodegradable microparticles for delivery of protein drugs, such as botulinum toxin, have been developed. The methods include the steps of precipitating and washing proteins with organic solvent to remove water prior to dispersing in polymer-dissolved organic solvent to prevent exposure to water/solvent interfaces and maintain bioactivity of the protein drugs and fabrication of microparticles by either template or emulsion method. Biodegradable microparticles, formed of one or more biodegradable polymers having entrapped in the polymer one or more protein agents, such as botulinum toxin, are also provided. Precipitated botulinum toxin and botulinum toxin-loaded microparticles can also be formulated into thermogels or crosslinked hydrogels. The stability of the protein within these microparticles, as well as the controlled release of the entrapped agents, provides for sustained efficacy of the agents.

47 Claims, 3 Drawing Sheets

(56) References Cited

U.S. PATENT DOCUMENTS

| | | | | |
|---|---|---|---|---|
| 7,588,172 | B2 ‡ | 9/2009 | Yamamoto | A61B 1/012 222/15 |
| 7,691,381 | B2 ‡ | 4/2010 | Hughes | A61P 25/06 424/18 |
| 8,226,598 | B2 ‡ | 7/2012 | Dunn | B01F 5/0685 604/82 |
| 8,501,187 | B2 ‡ | 8/2013 | Hughes | A61P 37/04 424/18 |
| 8,951,567 | B2 ‡ | 2/2015 | Park | A61K 9/1647 424/49 |
| 2005/0214326 | A1 ‡ | 9/2005 | Hunt | A61K 9/0019 424/239.1 |
| 2010/0226985 | A1 ‡ | 9/2010 | Van Tomme | A61K 9/0024 424/486 |
| 2010/0291027 | A1 ‡ | 11/2010 | Campbell | A61K 9/0019 424/85.2 |
| 2010/0310669 | A1 | 12/2010 | Paillard | |
| 2011/0293663 | A1 * | 12/2011 | Borodic | A61P 25/14 424/239.1 |
| 2012/0063997 | A1 ‡ | 3/2012 | Hunter | A61K 9/0019 424/1.11 |
| 2016/0128941 | A1 ‡ | 5/2016 | Park | A61K 9/1682 264/8 |
| 2016/0175410 | A1 ‡ | 6/2016 | Hunt | A61K 8/90 424/94 |

OTHER PUBLICATIONS

Acharya, et al., "The hydrogel template method for fabrication of homogeneous nano/microparticles", J Control Release, 141:314-9 (2010).

Aoki, "A comparison of the safety margins of botulinum neurotoxin serotypes A, B, and F in mice", Toxicon, 39:1815-20 (2001).

Aoki, "Preclinical update on Botox® (botulinum toxin type A)—purified neurotoxin complex relative to other botulinum neurotoxin preparations", Eu J Neurology, 6:s3-s10 (1999).

Chang and Patro, "Freeze-drying Process Development for Protein Pharmaceuticals", "Lyophilization of Biopharmaceuticals" (Costantino, H.R. and Pikal, M.J. eds) American Association of Pharmaceutical Scientists. 113-138 (2004).

He and Park, "Effects of the Microparticle Shape on Cellular Uptake", Mol. Pharm., 13:2164-71 (2016).

International Search Report for corresponding PCT application PCT/US2017/048174 dated Dec. 11, 2017.

Leader, et al., "Protein therapeutics: a summary and pharmacological classification", Nat Rev Drug Discovery, 7:21-39 (2008).

Lu, et al., "Microparticles produced by the hydrogel template method for sustained drug delivery", Int. J. Pharm., 461:258-69 (2014).

Neimann, et al., "Clostridial neurotoxins: new tools for dissecting exocytosis", Trends in Cell Biol. 4:179-85 (1994).

Schellmann, "Solvent denaturation", Biopolymers, 17:1305-22 (1979).

Sloop, et al., "Reconstituted botulinum toxin type A does not lose potency in humans if it is refrozen or refrigerated for 2 weeks before use", Neurology, 48:249-53 (1997).

Stewart, et al., "Interdomain zinc site on human albumin", PNAS, 11(7):3701-3706 (2003).

Van De Weert, et al., "Protein instability in poly(lactic-co-glycolic acid) microparticles", Pharm. Res., 17:1159-67 (2000).

Wang, et al., "Stabilization and encapsulation of human immunoglobulin G into biodegradeable microspheres", Journal of Colloid and Interface Science, 271(1):92-101 (2004).

Ye, et al., "Issues in long-term protein delivery using biodegradable microparticles", J. Control. Release, 156:241-60 (2010).

* cited by examiner
‡ imported from a related application form of microparticles, solid implants, or in situ forming # BIODEGRADABLE POLYMER FORMULATIONS FOR EXTENDED EFFICACY OF BOTULINUM TOXIN

CROSS-REFERENCE TO RELATED APPLICATIONS

This application is a continuation of U.S. Ser. No. 15/684,134, filed Aug. 23, 2017, which claims the benefit of and priority to U.S. Ser. No. 62/380,229, filed Aug. 26, 2016, and where permissible are hereby incorporated by reference in their entirety.

FIELD OF THE INVENTION

The invention is generally in the field of systems for drug delivery, and particularly biodegradable polymer formulations for the delivery of labile proteins such as botulinum toxin for a prolonged period of efficacy.

BACKGROUND OF THE INVENTION

Over the last several decades, thousands of sustained release drug delivery systems have been developed for enteral administration, especially via the oral route. However, since 1989 there have been only about 20 products approved for use in the clinic for delivering drugs as injectable long-term depot formulations (i.e., for weeks up to six months). Most injectable depot formulations are in the form of microparticles, solid implants, or in situ forming implants, and all injectable formulations currently in clinical use employ biodegradable polymers, so that the delivery systems do not have to be removed later.

To date the most widely used method for producing microparticle formulations is the double emulsion process (Ye et al., *Issues in long-term protein delivery using biodegradable microparticles*, J. Control. Release, 156, pp. 241-260 (2010)), where a drug is first dissolved in a suitable solvent (either water or an organic solvent depending on the drug solubility), and then added into the second solvent containing dissolved polymer, to make either a water-in-oil or oil-in-oil emulsion. For protein drugs, however, it has been a common practice to incorporate solid protein powders to make emulsions, because water-dissolved proteins are prone to denaturation upon exposure to the water/solvent interface (Ye et al., *J. Control. Release,* 156, pp. 241-260 (2010)). This emulsion process, however, presents formulation challenges due to the difficulty in uniformly dispersing protein powders into organic polymer solutions, and requires complicated manufacturing methods.

For example, the injectable formulation of the recombinant human growth hormone somatropin is formulated in PLGA microparticles and marketed as NUTROPIN DEPOT®. Somatropin is a protein of 191 amino acid residues, having a molecular weight of 22,124 Daltons. NUTROPIN DEPOT® was manufactured by the Alkermes' PROLEASE® process and approved by the U.S. Food and Drug Administration (FDA) in 1999. However, the production of NUTROPIN DEPOT® was discontinued in 2004 due to manufacturing difficulties.

In addition, the large and heterogeneous size of protein powders often renders them unsuitable for microparticle fabrication using existing methods. The final size of prepared PLGA microparticles is generally heterogeneous and big, requiring large-diameter gauge needles for injection. For example, microparticle formulations of somatropin (marketed as NUTROPIN DEPOT®), triptorelin (marketed as TRELSTAR®) and risperidone (marketed as RISPERIDAL CONSTA®) require needles having an outer diameter of 0.813 mm (i.e., 21-gauge or less). Delivery of the extended-release injectable formulation of naltrexone (marketed as VIVITROL®) requires a needle with outer diameter of 0.902 mm (i.e., 20-gauge). In comparison, delivery of insulin typically requires a needle having an outer diameter of 0.356 mm or less (i.e., 28-gauge, or greater).

In addition to microparticles or larger size solid implants, in situ forming polymer solutions have been used for long-term drug delivery (Dunn, et al., *Biodegradable in-situ forming implants and methods of producing the same,* U.S. Pat. No. 4,938,763 (1990); Dunn and Yarborough, *Coupling syringe system and methods for obtaining mixed composition,* U.S. Pat. No. 8,226,598 (2012)). For example, a drug and PLGA are dissolved in an organic solvent such as N-methyl-2-pyrrolidone (NMP), and the drug-PLGA solution is injected into the body. Subsequently, the solvent is removed in vivo from the formulation to the surrounding tissue, leaving a gel or solid biodegradable formulation. The in situ gel forming method, however, has been used only for small molecular drugs and peptide drugs which do not have the tertiary structure as proteins do.

Current manufacturing methods of formulating PLGA microparticles for extended-release of drugs have several disadvantages for protein drugs. A factor to consider in is the importance of maintaining the biological activity of the proteins, which can easily be denatured by changes in temperature, exposure to solvent-water interfaces, or exposure to water-air interfaces throughout the manufacturing process. Consequently, many protein drugs exhibit reduced efficacy following exposure to processes commonly employed in conventional manufacturing methods.

An exemplary protein drug is botulinum toxin. Botulinum toxin is an extremely potent neurotoxin produced by the bacterium *Clostridium botulinum*. Pharmaceutically acceptable amounts of botulinum toxin have been established for therapeutic and cosmetic purposes, and have an increasing number of applications in the biomedical and cosmetic industries. Botulinum toxins have been approved by the U.S. FDA for the treatment of neuromuscular disorders characterized by hyperactive skeletal muscles, including strabismus, blepharospasm, and hemifacial spasm as well as for the treatment of pain, urinary disorders, prostatic dysfunction, chronic migraines, sweating, etc. Botulinum toxin is also used in cosmetic applications to improve the appearance of wrinkles and glabellar frown lines. The effects of intramuscular injection of botulinum toxin typically occur within days following administration depending on the administered dose. Typically, botulinum toxin is formulated into an aqueous solution by reconstitution of a dry powder, e.g., in 0.9% sodium chloride, for use as a medical or cosmetic agent. However, the typical duration of symptomatic relief from a single intramuscular injection of botulinum toxin formulated in this manner averages about three-four months following administration. Because the risks of experiencing side-effects of medical or cosmetic application of botulinum toxin increase with the amount administered increases, the amount and regimen of administration currently limit the duration of efficacy of botulinum toxin for use in humans. The symptoms of toxicity of botulinum toxin can include nausea, difficulty walking and swallowing, and can progress to paralysis of respiratory muscles, and cardiac failure. The benefits of using toxin for various applications will increase if new delivery systems are available for maintaining the effect of toxin longer than what is currently available. Thus, there exists a need for improved methods of manufacturing improved extended release formulations that maintain the bioactivity of protein drugs, such as botulinum toxin.

There is also a need for improved methods of formulating high potency proteins such as botulinum toxin into sustained delivery systems, e.g., microparticles and gels, for delivery with very controlled pharmacokinetics and extended release. Most methods require uniform dispersion of active ingredient throughout the particle to get uniform release. This is a problem when the protein is very active, and therefore very small amounts are incorporated into the particles. Doses of all commercially available botulinum toxins are expressed in terms of units of biologic activity. One unit of botulinum toxin corresponds to the calculated median intraperitoneal lethal dose ($LD_{50}$) in female Swiss-Webster mice. BOTOX® (Allergan) is a sterile lyophilized form of botulinum toxin type A. It is produced from a culture of the Hall strain of *C. botulinum* and purified by a series of acid precipitations to a crystalline complex containing the toxin and other proteins. The specific activity of BOTOX® is approximately 20 Units/nanogram of neurotoxin protein complex. Each vial of BOTOX® contains 100 Units (U) of *Clostridium botulinum* type A neurotoxin complex, 0.5 milligrams of albumin (human), and 0.9 milligrams of sodium chloride in a sterile, vacuum-dried form without a preservative. The specific activity of botulinum toxin depends on the type and how it was prepared, and thus, different formulations may have different specific activities.

Therefore, it is an object of the invention to provide methods and compositions for the formulation of polymeric delivery systems, e.g., microparticles and gels, for extended release of protein drugs.

It is also an object of the invention to provide methods for the fabrication of delivery systems for the controlled release of protein active agents that exert minimal or no impact upon the biological activity of the protein active agents.

It is a further object of the invention to provide microparticles for the delivery of botulinum toxin for periods of time greater than achieved by current aqueous solution formulations.

It is a further object of the invention to provide systems that maintain the bioactivity of botulinum toxin and extend its efficacy in vivo.

It is yet a further object of the invention to provide compositions, methods, and devices for sustained release of protein active agents to a host subject following a single administration.

SUMMARY OF THE INVENTION

Methods for formulating polymeric microparticles for the delivery of potent protein or peptide active agents like botulinum toxins have been developed. The protein to be delivered will typically have a therapeutic, prophylactic or diagnostic activity requiring only small amounts of protein. The methods maintain the biological activity of protein active agents and facilitate controlled release of the proteins to enhance the efficacy in vivo. The method also improves pharmacokinetics through the judicious combination of stabilizing excipient which facilitates uniform dispersion of active in the microparticle, thereby significantly improving control and duration of release.

An exemplary protein active agent for delivery by the polymer microparticles is botulinum toxin which is a highly potent toxin, and which is notoriously hard to encapsulate for release with desired pharmacokinetics. Botulinum toxins that can be formulated into microparticles include botulinum toxin types A, B, C, D, E, F, G, and mixtures of these. Preferred botulinum toxins are botulinum toxin types A and B. In the preferred embodiment where nano-scale quantities of active agents, such as botulinum toxins, are required for clinical applications, the active agents are mixed with inert bulking agent prior to encapsulation. An exemplary protein bulking agent is human serum albumin (HSA). Surprisingly, the botulinum toxin, which is present in small quantity, mixes with the HSA, retains its activity, and disperses evenly in the microparticles, if processed as described below and in the examples.

Typically, the methods include the steps of (a) mixing dehydrated protein in an aqueous solution to form a protein solution; (b) precipitating the protein from the solution to form a precipitant; (c) washing the precipitant one or more times with a wash solvent to form a solvent-washed precipitant; (d) mixing or dispersing the solvent-washed precipitant in a solution containing a polymer to form a polymer-protein solution; and (e) preparing polymer microparticles encapsulating the protein from the polymer-protein solution by emulsifying with an emulsion solution. Washing the precipitated protein with solvent were found to be critical to obtaining the desired uniform encapsulation and controlled release, especially for botulinum toxin. Exemplary wash solvents include acetone, acetonitrile, dioxane, ethanol, 2-methoxy ethyl acetate, methoxy ethanol, ethoxy ethanol, butoxy ethanol, 2-propanol, propylene glycol methyl ether, ethanediol, 1,2-propanediol, tert-butyl alcohol, diethylene glycol, and combinations thereof. Exemplary emulsion solvents include benzyl alcohol, n-butyl acetate, chloroform, dioxane, dichloromethane, ethyl acetate, ethyl formate, methyl formate, phenethylamine, triacetin, and combinations. A preferred emulsion solvent is a combination of dioxane and dichloromethane.

Exemplary biocompatible polymers include polyhydroxyacids such as poly(lactides), poly(glycolides), and poly(lactide-co-glycolides), polycaprolactone, polyesteramides, polyanhydrides, poly(amino acids), polyorthoesters, polycyanoacrylates, poly(p-dioxanone), poly(alkylene oxalates), biodegradable polyurethanes, blends and copolymers thereof. A preferred biodegradable polymer is poly(lactide-co-glycolide), also known as poly(lactic acid-co-glycolic acid) or PLGA. In some embodiments the molecular weights and lactide:glycolide (L:G) ratios of polymers are selected to influence the physical properties of the microparticles, such as the release kinetics and duration of release of the entrapped active agents.

Microparticles formulated according to the methods are also provided. The particles are at least one micron in diameter and formed of one or more biodegradable polymers having entrapped in the polymer a protein therapeutic, prophylactic or diagnostic agent. In a preferred embodiment, the microparticles include botulinum toxin, HSA and PLGA. Typically, the quantity of the botulinum toxin associated with the microparticles is between about 1 unit and about 5,000 units of botulinum toxin, for example, the quantity of the botulinum toxin associated with the microparticles is between about 10 units and about 3,000 units of botulinum toxin A, between about 10 units and about 3,000 units of botulinum toxin B, or both. The amount of carrier, such as HSA, is usually orders of magnitude higher than that of botulinum toxin. For example, 100 units of botulinum toxin are diluted with between 0.5 and 1.0 mg of HSA.

In some forms, the biodegradable polymer formulations deliver drugs in an initial amount to produce an intended effect, and subsequently continue to release the drug for a desired period of time to maintain the effect for the desired time. Typically, the particles have a size in the micrometer or sub-micrometer range.

Diseases, disorders or cosmetic defects are treated by administering to a subject in need thereof an effective amount of the microparticles to reduce or prevent one or more symptoms of the disease, disorder or cosmetic defect in the subject. The microparticle formulations are preferably administered by injection. Typically, the polymeric microparticles enhance the biological activity of entrapped proteins to a greater extent than that of aqueous solution formulations containing an equivalent amount of the drug.

Microparticles eluting botulinum toxin can be used for treatment of muscle stiffness/spasms or movement disorders (such as cervical dystonia, torticollis), treatment of uncontrollable sweating, to enhance the cosmetic appearance of wrinkles, and to prevent headaches in people with very frequent migraines.

DETAILED DESCRIPTION OF THE INVENTION

I. Definitions

Figure 1:
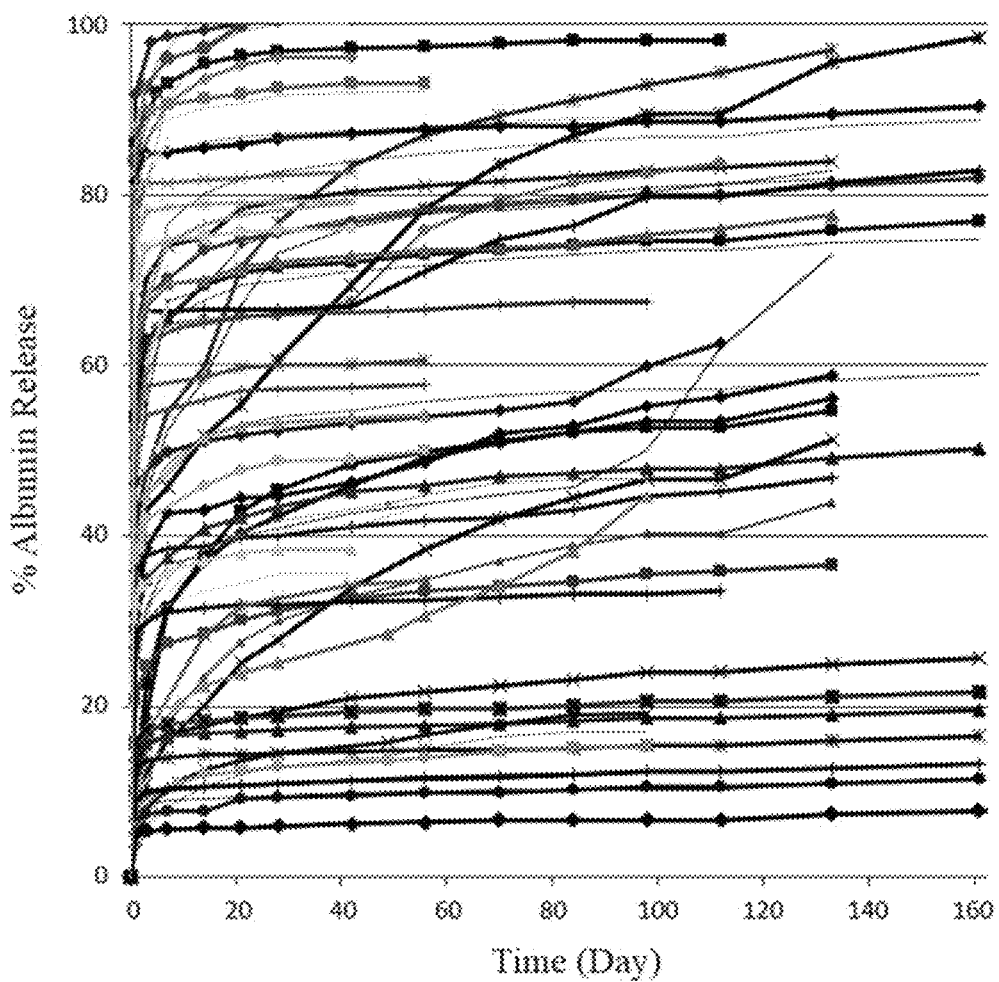
FIG. 1 is a line graph showing the relative amounts of albumin released from microparticles (% of total) as a function of time (days) for each of 78 different formulations of microparticles including PLGAs with different molecular weights, different lactide:glycolide (L:G) ratios, and different end groups, respectively.

The term "effective amount" or "suitable amount" is the minimum concentration required to effect a measurable improvement or prevention of any symptom or a particular condition or disorder, to effect a measurable enhancement of life expectancy, or to generally improve patient quality of life. The effective amount is dependent upon the specific biologically active molecule and the specific condition or disorder to be treated. Effective amounts of many proteins, such as botulinum toxin or monoclonal antibodies, are well known in the art.

The "median effective dose" is the dose that produces a quantal effect (all or nothing) in 50% of the population that takes it (median referring to the 50% population base). It is also sometimes abbreviated as the $ED_{50}$, meaning "effective dose, for 50% of people receiving the drug". The $ED_{50}$ is commonly used as a measure of the reasonable expectancy of a drug effect, but does not necessarily represent the dose that a clinician might use. This depends on the efficacy and toxicity. The toxicity and lethality of a drug can be quantified by the $TD_{50}$ and $LD_{50}$, respectively. Ideally, the effective dose would be substantially less than either the toxic or lethal dose for a drug to be therapeutically relevant.

The terms "thermogel", "thermosensitive polymer" and "thermoresponsive polymer" are used interchangeably and refer to polymers that remain dissolved in aqueous solution at lower temperatures, such as room or refrigerator temperatures, but precipitate into the gel state at higher temperatures, e.g., 30° C., or body temperature. Thermogels are typically block copolymers consisting of hydrophilic and hydrophobic blocks, such as poly(ethylene glycol) (PEG) and PLGA, respectively. The balance between the two blocks determines the gelation temperature, i.e., the temperature at which an aqueous solution becomes a gel.

As used herein "treatment" or "treating" means to administer a composition to a subject or a system with a disease, disorder, or cosmetic defect to reduce the severity or onset of one or more symptoms, of the disease or disorder. "Prevention" or "preventing" means to administer a composition to a subject or a system at risk for a disease, disorder or cosmetic defect, such as wrinkles.

As used herein, "microparticles" refers to particles having a diameter between one micron and 400 microns, typically less than 200 microns, more typically less than 150 microns, most preferably for the uses described herein in the range of less than 100 microns in diameter. Microparticles include microcapsules, microcarriers, microvehicles, microstructures, and microspheres unless otherwise specified.

The term "biocompatible" refers to one or more materials that are neither themselves toxic to the host (e.g., an animal or human), nor degrade to release toxic components in the host.

The term "pharmaceutically acceptable carrier" includes solvents, dispersion media, pH buffering agents, inert bulking agents, and other materials such as those listed by the U.S. FDA as Generally Regarded as Safe (i.e., "GRAS").

II. Microparticles

Typically, the microparticles include (1) one or more biodegradable polymer(s); and (2) one or more labile active agents. The microparticles are optionally formulated with one or more additional active agents and/or pharmaceutically-acceptable excipients.

A. Polymers

The polymer microparticles are preferably formulated from non-toxic, non-immunological, biocompatible polymers. Exemplary biodegradable polymers include poly(lactide-co-glycolide) (PLGA), poly(lactic acid) or polylactide (PLA), and poly(ε-caprolactone) (PCL), poly(glycolic acid) or polyglycolide (PGA), poly(D-lactic acid) or poly(D-lactide) (PDLA), poly(L-lactic acid) or poly(L-lactide) (PLLA), polyanhydrides, poly(ortho esters), collagen and cellulosic derivatives and hyaluronic acid.

In some forms, the biodegradable polymers are selected to form mixtures of two or more different polymers. For example, in some forms, biodegradable polymers are selected to exhibit specific functional properties when combined. For example, in some embodiments two or more biodegradable polymers are combined to form thermosensitive or thermo-responsive microparticles.

Microparticles can be made using a variety of polymers, both synthetic (e.g., PLGA) and natural (e.g., hyaluronic acid). Structural parameters of polymers, such as molecular weight, lactide:glycolide (L:G) ratio and relative concentration are selected to provide desired functions, such as solution-gel transition temperature, degradation kinetics (e.g., time to degrade in vivo), protein-loading efficacy and bioreactivity (e.g., toxicity and immunological reactivity in vivo).

Biodegradable PLGA microparticles can be made to control degradation and release over periods of time ranging from days, weeks or months in vivo after subcutaneous or intramuscular administration. For example, the release of proteins from microparticles (i.e., delivery in vivo), as measured for example by albumin release, is a function of the L:G ratio. In other embodiments, the release of proteins from microparticles is governed by more than one factor. In some embodiments, the release of proteins from microparticles formulated according to the emulsion method is governed by both the solvent composition and L:G ratio and molecular weight of the polymer used.

In some embodiments the release of proteins occurs in a continuous manner. In other embodiments the release of proteins occurs in a biphasic or multi-phasic manner. For example, in some embodiments, the initial burst release decreases as the lactide content of PLGA increases. In further embodiments, the overall release rate is dependent on the solvent used for making microparticles.

The molecular mass of polymers used to fabricate microparticles can be selected to provide microparticles having desired polymer characteristics. The polymer microparticles are preferably formulated from polymers having a weight average molecular weight ($M_w$) of between approximately 1,000 Daltons (Da) and 1,000,000 Da, inclusive.

An exemplary physical property of a polymer that can vary according to molecular weight is temperature-sensitivity. For example, a polymer can exist as a solid or liquid, or can transition from a solid state to a liquid state according to a given temperature as determined by the molecular weight and composition of the polymer. Polymers and compositions of polymers that have a solution-gel transition point associated with a given temperature range are referred to as thermogels. In some embodiments, the polymers used to formulate sustained release delivery systems are selected based on the gelling temperature of the polymers. For example, the solution-gel transition temperature of the thermosensitive polymers is a function of the one or more polymers used to formulate the thermogel. In some embodiments two or more polymers having different gelling temperatures are combined to form thermogels having a desired solution-gel transition temperature. Exemplary gelling temperatures are above 0° C. and typically above 4° C., such as 10° C., or greater than 10° C. up to 40° C., or above 40° C. In a preferred embodiment, microparticles are formulated to have a gelling temperature below the typical body temperature of a healthy human, such as below 37° C.

Exemplary polymers for use as thermogels include PLGA-PEG-PLGA block copolymers, for example, those presented in Table 1, below.

TABLE 1

Examples of Thermogels

| Thermogel Polymers (PLGA-Based) | L:G Ratio (W/W) | Mol. Wt. (Da) | $T_{sol-gel}$ (° C.) |
| --- | --- | --- | --- |
| PLGA-PEG-PLGA (AK012) | 50:50 | 1,000-1,000-1,000 | >12.5 |
| PLGA-PEG-PLGA (AK019) | 50:50 | 1,500-1,500-1,500 | >27.5 |
| PLGA-PEG-PLGA (AK024) | 75:25 | 1,100-1,000-1,100 | >15.0 |
| PLGA-PEG-PLGA (AK085) | 50:50 | 1,400-1,500-1,400 | >32.5 |
| PLLGA-PEG-PLLGA (AK087) | 75:25 | 1,100-1,000-1,100 | >17.5 |
| PLGA-PEG-PLGA (AK091) | 86:14 | 1,500-1,500-1,500 | >30.0 |
| PLGA-PEG-PLGA (AK097) | 94:06 | 1,700-1,500-1,000 | >27.5 |
| PDLL-PEG-PDLL (AK100) | 100:0 | 1,700-1,500-1,700 | >30.0 |
| PDLL-PEG-PDLL (AK046) | 100:0 | 1,000-1,000-1,000 | >17.5 |

| Thermogel Polymers (Caprolactone-Based) | CL:L Ratio (W/W) | Mol. Wt. (Da) | $T_{sol-gel}$ (° C.) |
| --- | --- | --- | --- |
| PLCL-PEG-PLCL (AK108) | 75:25 | 1,600-1,500-1,600 | >30.0 |
| PLCL-PEG-PLCL (AK109) | 60:40 | 1,700-1,500-1,700 | >30.0 |
| mPEG-PCL (AK036) | 100:0 | 750-2,500 | >15.0 |
| PCL-PEG-PCL (AK035) | 100:0 | 1,000-1,000-1,000 | >12.5 |

$T_{sol-gel}$: Sol-Gel Transition Temperature; PDLL: poly(DL-lactide); P(LCL): Poly(lactide-co-caprolactone); mPEG: methoxy PEG; PCL: polycaprolactone; PLLGA-PEG-PLLGA: L-chiral lactide in PLGA-PEG-PLGA, and otherwise is DL racemic; CL:L: caprolactone: lactide. AK series polymers are from Akina PolySciTech.

Polymers for use as thermogels are commercially available from Akina PolySciTech (West Lafayette, Ind.). The dissolution of dried thermogel polymer in water usually takes a day but it can occur faster by the addition of a small amount of biocompatible water-miscible solvent. Notably, the addition of poly(ethylene glycol) of low molecular weight can be added to the dried polymer to improve the rate of subsequent solubilization in water. For example, the addition of PEG 400 Da, in a ratio of 25:75, to poly(lactide-co-caprolactone)-b-poly(ethylene glycol)-b-poly(lactide-co-caprolactone) (AK109 from Akina PolySciTech) can decrease the aqueous dissolution time from more than a day to 2 hours for generating a thermogelling solution.

B. Therapeutic, Prophylactic and Diagnostic Agents

Therapeutic, prophylactic and diagnostic agents can be encapsulated into particles. These can be proteins or peptides, nucleic acids, lipids, sugars or polysaccharides, small molecules (molecular weight typically less than 1,000 Da), or combinations thereof. It is particularly well suited to labile agents, especially those which are hydrolytically unstable.

The method has been tested as applied primarily to botulinum toxin, however, it has applicability to other biological and/or macromolecular based therapeutic entities such as human growth hormone (rHGH), human insulin, follicle-stimulating hormone (FSH), erythropoietin (EPO), granulocyte colony-stimulating factor (G-CSF), alpha-galactosidase A, alpha-L-iduronidase, tissue plasminogen activator (TPA), flucocerebrosidase, interferons, insulin-like growth factors antibodies, cytokines, and vaccines. Additionally, peptides, deoxyribonucleic acids (DNA), ribonucleic acids (RNA), and silencing ribonucleic acids (siRNA) as well as other labile agents. These agents can be co-precipitated along with a carrier protein prior to incorporation into the polymer microparticle. Based on the therapeutic agent of choice, the resulting formulation can be used for a wide range of therapeutic, prophylactic, and/or diagnostic applications.

In certain embodiments, only one active agent is incorporated into the drug eluting microparticles. In some embodiments, two or more protein active agents are incorporated within the same drug eluting microparticles. In other embodiments, one or more protein active agents and one or more non-protein active agents are incorporated within the same drug eluting microparticles.

Generally, the methods of making biocompatible microparticles do not impose any limitation on the structure of the encapsulated protein agent that is to be delivered by the microparticles. For example, proteins formulated within microparticles can have a mass of between 3,000 Da and 1 million Da, or more, and can be of any amino acid sequence.

A biologically active agent is a substance that, for example, is used for the treatment, prevention, diagnosis, cure, or mitigation of disease or disorder, affects the structure or function of the body, region, or site therein, or becomes biologically active or more active upon exposure to a predetermined physiological environment (such as a prodrug). Agents may be biologically, physiologically, or pharmacologically active substances that act locally or systemically in the human or animal body.

The active agent to polymer ratio (unit or mg of active agent per mg of polymer) can be controlled to regulate the overall dose, efficacy and release rate of the active agent. Suitable polymer to active agent ratios include, but are not limited to: 1000:1, 100:1, 10:1, 1:1, inclusive (unit of active agent per mg of polymer). The preferred ratio is approximately 100 unit botulinum toxin:1 mg of microparticles.

Preferred bioactive agents are polypeptides, such as protein drugs. Exemplary protein drugs that can be incorporated into the described microparticles include botulinum toxin.

1. Botulinum Toxin

A preferred protein drug is for use with the described drug eluting microparticles is botulinum neurotoxin produced by the anaerobic, gram positive bacterium *Clostridium botulinum* and related species.

Botulinum toxin has a molar mass of approximately 150,000 g/mol (for heavy and light chains toxin alone) and is a potent neurotoxin, which causes a neuro-paralytic illness in humans and animals referred to as botulism. The molecular weight of the complex form of botulinum toxin has the molecular weight of between approximately 600,000 and 900,000 g/mol.

The effects of botulism typically appear 18 to 36 hours after eating the foodstuffs infected with a *C. botulinum* culture or spores. The botulinum toxin can apparently pass attenuated through the lining of the gut and attack peripheral motor neurons. Symptoms of botulinum toxin intoxication can include nausea, difficulty walking and swallowing, and can progress to paralysis of respiratory muscles, cardiac failure and death.

Neurotransmitters are packaged in synaptic vesicles within the cytoplasm of neurons and are then transported to the inner plasma membrane where the vesicles dock and fuse with the plasma membrane. Studies of nerve cells employing clostridial neurotoxins as probes of membrane fusion have revealed that fusion of synaptic vesicles with the cell membrane in nerve cells depends upon the presence of specific proteins that are associated with either the vesicle or the target membrane. These proteins have been termed SNAREs. A protein alternatively termed synaptobrevin or VAMP (vesicle-associated membrane protein) is a vesicle-associated SNARE (v-SNARE). There are at least two isoforms of synaptobrevin; these two isoforms are differentially expressed in the mammalian central nervous system, and are selectively associated with synaptic vesicles in neurons and secretory organelles in neuroendocrine cells. The target membrane-associated SNAREs (t-SNARES) include syntaxin and SNAP-25. Following docking, the VAMP protein forms a core complex with syntaxin and SNAP-25; the formation of the core complex appears to be an essential step to membrane fusion (Neimann, et al., *Trends in Cell Biol.* 4:179-185 (1994)).

Various PLGA formulations containing botulinum toxin have been described, but the efficacy of the botulinum toxin encapsulated in the PLGA microparticles has not been demonstrated (Donovan, Botulinum toxin implant, U.S. Pat. No. 6,312,708 (2001); Donovan, Biodegradable botulinum toxin implant, U.S. Pat. No. 6,506,399 (2003); Donovan and Brady, Neurotoxin implant, U.S. Pat. No. 6,306,423 (2001); Donovan and Brady, Biodegradable neurotoxin implant, U.S. Pat. No. 6,383,509 (2002); Donovan and Brady, Controlled release neurotoxin system, U.S. Pat. No. 6,585,993 (2003); Hughes and Olejnik, Stabilized biodegradable neurotoxin implants, U.S. Pat. No. 7,691,381 (2010); Hughes and Olejnik, Stabilized biodegradable neurotoxin implants, U.S. Pat. No. 8,501,187 (2013)).

The commercially available form of botulinum toxin for use in medical and cosmetic application is marketed as BOTOX®, DYSPORT®, XEOMIN®, which are a freeze-dried, purified botulinum toxin with albumin and other excipients. The botulinum toxin type A is made from a culture of the Hall strain of *Clostridium botulinum*. The botulinum toxin type A complex is purified by a series of acid precipitations to a crystalline complex which is re-dissolved in a solution containing saline and albumin before vacuum-drying. The vacuum-dried product is stored in a freezer at or below −4° C. BOTOX®, DYSPORT®, XEOMIN® and other products can be reconstituted with sterile, non-preserved aqueous solution prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® retains its potency for at least two weeks. Neurology, 48:249-53:1997.

The spores of *Clostridium botulinum* are found in soil and can grow in improperly sterilized and sealed food containers of home based canneries, which are the cause of many of the cases of botulism.

Botulinum toxin is available from multiple commercial sources. Type A complex from *Clostridium botulinum* available from List Biological Laboratories, Inc. (Campbell, Calif.). The toxin is soluble and 100 µg is dissolved readily into 1 mL of suitable aqueous buffer. Solutions of botulinum toxin can be made into aliquots and frozen.

2. Other Protein Active Agents

The microparticles can deliver hormones, antibodies, growth factors, cytokines, immunomodulators, integrins and toxins. A comprehensive listing of protein active agents is provided in Leader, et al., (Nature Reviews Drug Discovery (7) pp. 21-39 (2008), and references therein), the content of which is incorporated by reference.

Exemplary protein drugs that can be formulated or reformulated into polymer microparticles using the described methods include somatropin (NUTROPIN DEPOT®). Exemplary peptide drugs can be formulated or reformulated into polymer microparticles using the described methods include leuprolide (LUPRON DEPOT® and ELIGARD®), goserelin (ZOLADEX® DEPOT), octreotide (SANDOSTATIN LAR® DEPOT), triptorelin (TRELSTAR DEPOT®), Buserelin, lanreotide (SOMATULINE® DEPOT), exenatide (BYDUREON®), and pasireotide (SIGNIFOR® LAR).

Other protein drugs that can be formulated into the polymer microparticles formulated according to the described methods include, but are not limited to, insulin and insulin analogues, growth hormone somatotropine, mecasermin, beta-gluco-cerebrosidase, alglucosidase-alfa, adenosine deaminase, erythropoietin, interferons, L-asparaginase, and ranibizumab (e.g., LUCENTIS®).

A non-limiting list of anti-cancer protein therapeutic agents includes Bevacizumab (e.g., AVASTIN®), Cetuximab (e.g., ERBITUX®), Panitumumab (e.g., VECTIBIX®), Alemtuzumab (e.g., CAMPATH®), Rituximab (e.g., RITUXAN®), and Trastuzumab (e.g., HERCEPTIN®).

A non-limiting list of immuno-regulatory protein therapeutic agents includes abatacept (ORENCIA®), anakinra (ANTRIL®, KINERET®), adalimumab (HUMIRA®), etanercept (ENBREL®), infliximab (REMICADE®), alefacept (AMEVIVE®), efalizumab (RAPTIVA®), natalizumab (TYSABRI®), eculizumab (SOLIRIS®), antithymocyte globulin (rabbit) (THYMOGLOBULIN®), basiliximab (SIMULECT®), daclizumab (ZENAPAX®), and muromonab-CD3 (ORTHOCLONE®, OKT3®).

3. Diagnostic and Accessory Agents

The microparticles can deliver protein diagnostic and/or accessory agents having a broad range of activities, including in vivo diagnosis of diseases and disorders, imaging agents, hormones that influence or control biological functions, proteins that are useful for ex vivo analytical or diagnostic methods, and proteins useful as chaperones to stabilize other active agents, catalyze or elicit conversion of other active agents from an inactive to an active state or vice-versa, buffering agents and filling agents.

The microparticles can deliver non-protein active agents, alone or in combination with one or more protein active agents. Non-protein active agents that can be delivered via polymeric microparticles include, but are not limited to, small molecules, carbohydrates, polysaccharides, nucleotides, oligonucleotides, and lipids. Exemplary small molecule active agents include organic and organometallic compounds. Exemplary biomacromolecules include nucleic acids. The active agents can be hydrophilic, hydrophobic, or amphiphilic.

Exemplary bioactive agents can include, but are not limited to, anti-inflammatory agents, immuno-modulatory agents, molecules that promote cell migration, molecules that promote or retard cell division, molecules that promote or retard cell proliferation and differentiation, molecules that stimulate phenotypic modification of cells, molecules that promote or retard angiogenesis, molecules that promote or retard vascularization, molecules that promote or retard extracellular matrix disposition, signaling ligands, anesthetics, antibiotics, steroids, and chemotherapeutic agents.

Exemplary non-protein diagnostic agents include paramagenetic molecules, fluorescent compounds, magnetic molecules, radionuclides, X-ray imaging agents, and MRI contrast agents.

III. Methods of Making Drug Eluting Microparticles

Methods of making biocompatible microparticles that enhance the efficacy of encapsulated protein drugs, including botulinum toxin, after loading into biodegradable polymers have been established. The methods include combining a non-aqueous solution of biodegradable polymers with one or more protein active agents mixed with a bulking agent such as albumin and washed in non-aqueous solvents, then producing microparticles by microfabrication or emulsion methods. Typically, the methods produce biocompatible microparticles containing encapsulated protein agents, such as botulinum toxin. The methods can be used for the large-scale production of controlled-release delivery systems of botulinum toxin in vivo. The microparticles containing therapeutic, prophylactic and diagnostic proteins can be administered using routine techniques.

The methods include formulating protein-loaded microparticles using an emulsion of water ("W") and/or one or more non-aqueous solvents or oils ("O"). In an exemplary embodiment, the methods include adding an emulsion of W/O or O/O to a large quantity of water to form W/O/W or O/O/W double emulsion. The methods of using protein precipitates overcome loss of activity of protein active agents associated with denaturation of water-dissolved proteins that occurs at the interface between water and an organic solvent.

The methods include the steps of (a) precipitation of active agents mixed with a bulking agent to produce a protein precipitant; (b) washing of protein precipitants to produce a solvent-washed precipitant; (c) alternatively reducing the size of solvent-washed precipitants by wet milling or reducing the size of freeze-dried precipitants by dry milling or cryomilling, (d) dispersing the precipitant in a polymer; and (e) fabricating the microparticles by microfabrication or emulsion methods. Each of the method steps is described in greater detail, below.

A. Precipitation of Therapeutic, Prophylactic or Diagnostic Agents ("Active Agents")

Proteins for formulating within biocompatible polymers are provided as dry powders and dissolved in an aqueous solution, then precipitated. Additional stabilizing agents can be added to the aqueous solution to improve the stability of the protein precipitate.

1. Providing Dehydrated Protein

Typically protein active agents for use in the methods are provided in dehydrated form, for example, as a dried powder. Dehydration can be carried out using known methods, such as lyophilization, spray-drying, and spray freeze-drying. Typically, methods for lyophilization of proteins are carried out in three steps, including (1) freezing (which involves freezing the product and creating a solid matrix suitable for drying); (2) primary drying (which involves the removal of ice through sublimation by reducing the pressure of the product environment while maintaining the product temperature at a low target level); and (3) secondary drying (which includes removal of bound water until the residual moisture content reaches its targeted level). A comprehensive guide to the processes of drying proteins is provided in Chang and Patro (Freeze-drying Process Development for Protein Pharmaceuticals, in *Lyophilization of Biopharmaceuticals*, American Association of Pharmaceutical Scientists, pp. 113-138 (2004)).

In an exemplary method, dehydration removes 90-100% of the water from the protein. Typically, the dehydration process is carried out in a manner that does not reduce or otherwise alter the biological activity of the protein. When two or more proteins are used, the proteins can be combined prior to, or after, dehydration.

Suitable bulking/carrier materials include various proteins such as albumin, gelatin, or transferrin, and polymers such as polyvinylpyrrolidone or hydroxypropyl methylcellulose. The most common bulking/carrier protein applied for botulinum toxin is albumin.

a. Preparation of Botulinum Toxin

In an exemplary embodiment, the protein active agent is botulinum neurotoxin Type A complex (i.e., botulinum toxin) from *Clostridium botulinum* (*C. botulinum*), which has extremely high potency and toxicity in humans.

b. Preparation of Bulking Agents

When an active agent is required in extremely small quantities, for example, an active agent that has extremely high activity and/or high toxicity, such as botulinum toxin, one or more additional excipients, such as polypeptides or proteins, can be included as a bulking agent or carrier. Since protein drugs are often highly potent, very small quantities are typically required to achieve a desired effect. In the absence of an excipient or bulking agent it can be impractical to develop and produce suitable delivery systems. Therefore, in some forms, where nano-scale quantities of active agents, such as botulinum toxins, are required for clinical applications, the active agents are diluted, for example, by mixing with inert bulking agents.

An exemplary bulking agent protein for use with botulinum toxin is human serum albumin ("HSA") or albumin. In an exemplary embodiment, a stock solution of the toxin (100 μg) is diluted in a suitable aqueous buffer, such as Tris buffer, to yield a working solution, for example, a 100 μL aliquot containing 10 μg toxin (or approximately 10,000 Mouse Units). This solution is mixed with the bulking agent protein (e.g., HSA) to make a solution of 50 mg/mL in 50 mM Tris-HCl pH 7.5.

2. Selection of a Precipitant

In some embodiments, the methods include the step of selecting suitable reagents and conditions for precipitating one or more protein active agents.

For example, when the active agent is botulinum toxin, and the bulking agent is albumin (toxin/albumin), various agents can be tested for their ability to precipitate toxin/albumin from aqueous solution.

In an exemplary method, precipitates are identified by labeling the protein, for example, using fluorescein isothiocyanate (FITC-labelling). Typically, when bulking agent is used, the bulking agent is labelled for ease of interpretation. For example, when the active agent is botulinum toxin, and the bulking agent is albumin (toxin/albumin), the majority of the protein in the toxin/albumin mixture is albumin, and agents are screened for the ability to precipitate albumin.

Exemplary precipitants include, but are not limited to, salts such as zinc chloride ($ZnCl_2$), polymers such as polyethylene glycol (PEG), solvents, ion pairs, amino acids, and fatty acids. Specific examples of precipitants are L-histidine methyl ester, L-cysteine ethyl ester, Nα-(tert-butoxycarbonyl)-L-asparagine, L-proline benzyl ester, N-acetyl-L-tryptophan, gentisic acid, pentetic acid, octanoic acid, and zinc chloride.

In some embodiments, precipitants are selected for the ability to precipitate more than one agent using more than a single round of screening. For example, when bulking agent is used, a first round of screening is performed to identify one or more agents suitable for precipitating the bulking agent, followed by a second or further round of screening to determine whether these same agents are suitable for precipitating the bulking agent in combination with one or more active agents or other excipients. For example, when the active agent is botulinum toxin, and the bulking agent is albumin (toxin/albumin), the agents identified as having the ability to precipitate albumin are subsequently screened for the ability to precipitate the toxin/albumin mixture.

Factors that determine the selection of a suitable precipitant include the ability to produce precipitants having properties suitable for subsequent processes, such as desirable size and density, as well as maintaining the bioactivity of the active agent.

When the active agent is botulinum toxin, and the bulking agent is albumin (toxin/albumin), a preferred precipitant is zinc chloride. In an exemplary method, the final concentration of zinc chloride used is approximately 1% weight to volume (w/v).

Following addition of the selected precipitant, the supernatant is removed, for example, by centrifugation, to collect the precipitated protein.

3. Enzyme Assay of Botulinum Toxin for Biological Activity

Steps involved in incorporating proteins into polymeric microparticles often denature proteins, and result in loss of bioactivity (Schellman, *Biopolymers*, 17, pp. 1305-1322 (1978); van de Weert, et al., *Pharm. Res.*, 17, pp. 1159-1167 (2000)). Therefore, the methods can optionally include tests to determine whether precipitation impacts the biological activity of an active agent.

In an exemplary embodiment, when the protein is botulinum toxin and albumin (toxin/albumin), a preferred biological test is measurement of toxin activity by the fluorescence resonance energy transfer (FRET) SNAP-25 Endopeptidase Assay. Botulinum toxin is a zinc-dependent endopeptidase that cleaves proteins required for neurotransmitter release. One of the substrates for toxin endopeptidase activity is the synaptosome-associated protein of 25 kDa (SNAP-25). Therefore, in an exemplary embodiment, the FRET SNAP-25 endopeptidase assay kit (Biosentinel's Botest) is used to measure the ability of toxin to proteolytically cleave the natural SNAP-25 substrates. The SNAP-25/ endopeptidase assay measures the action of toxin on its target molecule, SNAP-25, and this is a potential in vitro replacement test method. The FRET assay allows for detection of toxin activity without using the mouse paralysis study, allowing testing of many toxin formulations.

In an exemplary method, Zn-precipitated toxin/albumin is prepared and divided into aliquots. Some samples are stored in a refrigerator as a control and other samples are washed with organic solvents for solvent washing. All samples are added with 500 μL of 100 mM EDTA while vortexing to dissolve the toxin/albumin precipitate. The dissolved toxin/albumin is transferred to a centrifugal filter device (e.g., Millipore, Mw cut off 10,000 Da), the filter device is centrifuged and pure water is added to remove EDTA and zinc chloride.

After removing filtrate, toxin/albumin is buffer exchanged into 50 mM Tris pH 7.5, recovered into a clean microtube and tested for enzymatic activity using the FRET assay (BoTest kit from BioSentinel, Inc.).

B. Solvent Washing of Proteins

The solvent washing process includes the step of washing the precipitated proteins using a selected solvent. Typically, solvent washing steps enhance the loading and homogeneous distribution of protein active agents in polymeric microparticles.

Following precipitation and removal of the supernatant from the precipitated protein, any remaining water is removed, for example, by mixing with a water-miscible solvent. Typically, one or more water-miscible solvents are added to the precipitated protein at a suitable volume ratio to remove residual water from the precipitate. Water-miscible solvents can be added to the precipitated protein at a volume ratio of at least 1:1, for example, 5:1, 10:1, or higher than 10:1. Mixing of solvent solutions is carried out by vortexing or stirring.

1. Selection of Wash Solvents

Suitable solvents that can be used to remove water include those which maintain the biological activity of protein active agents. Therefore, the methods can include the step of screening water-miscible solvents for removing water from precipitated proteins. Exemplary solvents include acetone, acetonitrile, dioxane, ethanol, 2-methoxy ethyl acetate, methoxy ethanol, ethoxy ethanol, butoxy ethanol, 2-propanol, propylene glycol methyl ether, ethanediol, 1,2-propanediol, tert-butyl alcohol, diethylene glycol, methanol, N-methylpyrrolidone, dimethylacetamide, dimethylformamide, dimethylsulfoxide, pyridine, tetrahydrofuranacetonitrile, etc. Preferably, water-miscible solvents have low viscosity, to facilitate the isolation of solvent-washed precipitate by centrifugation or diafiltration.

2. Recovery of Solvent-Washed Proteins

Solvent-washed protein precipitates can be collected using any suitable means, such as by centrifugation. The solvent-washed protein precipitate is subsequently mixed with polymer (e.g., PLGA solution in dioxane, dichloromethane, n-butyl acetate, or other solvent) to make microparticles. This solvent washing process allows preparation of PLGA microparticles by emulsion or microfabrication methods, maintaining the bioactivity of toxin. In some embodiments, the solvent-washed protein powder is freeze-dried.

In an exemplary embodiment, solvent-washed botulinum toxin/albumin precipitate is collected by centrifugation at 4,500-5,000 relative centrifugal force (rcf) for one minute or longer depending on the volume of a sample. A flat bottom centrifugal container is preferred.

C. Size-Reduction of Protein Powder

The methods can include the step of grinding the freeze-dried protein powder to create particles having a smaller size than that resulting directly from the drying process. Typically, freeze-dried protein powder is ground into particle of micrometer and sub-micrometer sizes.

Exemplary methods of grinding powder include grinding by hand, for example, using a pestle and mortar, or grinding using automated means, for example using grinding balls as implemented within a planetary ball mill machine (Changsha Deco Equipment Co., China) or CryoMill (Retsch). In an exemplary embodiment, grinding balls for use in an automated milling process are made of zirconuium oxide, stainless steel, agate, tungsten, alumina or variable plastics such as Teflon (polytetrafluoroethylene; PTFE). Typically, protein powders are subjected to size-reduction by milling in the absence (dry milling), or presence (wet milling) of a solvent. Dry milling may be performed in the presence of a temperature-controlling agent as described in next section.

1. Dry Milling

Protein powders for use in the described methods is ground for a suitable time to yield powder having particles of desired average powder size, using standard "dry" milling methods. Dry milling can be carried out using manual or automate methods. An exemplary powder size produced by hand-milling is about 10 µm. An exemplary powder size produced by automated processes, such as planetary ball milling, is about 1 micron or less. Grinding times can be selected according to the amount of starting material and the desired particle size, for example, from a few minutes to several hours.

The grinding of protein powders can result in an increase in the temperature of powder, which can result in changes in the protein state and potentially lead to reduction in biological activity. Therefore, in some embodiments, grinding is carried out in a temperature controlled environment, for example, at 4° C. In some embodiments, temperature control of the protein powder throughout the grinding process is implemented by the grinding apparatus itself. In a particular embodiment a refrigerant such as ice, dry ice, or liquid nitrogen is placed in proximity to the grinding vessel to counteract any increases in heat associated with grinding. For example, when automated grinding equipment is used, a chamber can be used to hold ice, dry ice, or liquid nitrogen around the milling container so that the temperature was maintained low during planetary ball milling. Alternatively, cryomilling using CryoMill (Retsch) was also used to produce submicron size protein powders.

Preferably, grinding of protein powders maintains the biological activity of the protein.

2. Wet Milling

In some embodiments, protein powders are ground for a suitable time to yield powder having particles of desired average powder size in the presence of a solvent (i.e., "wet milling"; "wet grinding"). Wet milling can prevent increases in temperature that can lead to a reduction in efficacy of the protein, for example, when ground in the dry state (i.e., in the absence of a solution or a cooling agent). Therefore, wet milling methods represent an alternative means to dissipate heat generated by grinding and avoid heat-induced deactivation of proteins, such as botulinum toxin.

Solvents useful for wet milling of protein powders can be selected based on the characteristics of the protein powder. Exemplary solvents include, but are not limited to organic solvents acetone, acetonitrile, n-butyl acetate, dioxane, dichlomethane and ethyl acetate. Other suitable organic solvents can be seen in Table 7.

In an exemplary method of wet milling, grinding balls of different diameter sizes (e.g., 10 mm, 5 mm and 1 mm, respectively) and the protein powder are mixed with an organic solvent in a solvent-resistant container of an appropriate size, for example, a 30 mL Teflon container. The container is mounted on a milling machine and rotated at a suitable speed (e.g., 300-900 revolutions per minute; rpm) for a suitable period of time (e.g., 1-6 hours). Particles prepared by hand grinding, planetary ball milling, cryomilling, and solvent washing are suitable to make microparticle and gel formulations.

In a particular embodiment, botulinum toxin/albumin protein powder is ground to a particle size of less than 1 micrometer while suspended in organic solvent using a combination of hand grinding and/or planetary ball milling.

D. Microparticle Fabrication

The methods include the step of fabricating the microparticles. Preferably, methods of fabricating microparticles using solvent-washed protein powder avoid denaturing or deactivation of the protein that occurs upon exposure of water-dissolved protein to the air-water-solvent interface.

Several microfabrication techniques have been developed to make microparticles for drug delivery applications, including micro-imprint lithography, solvent-assisted micromolding, micro-fluidic contact printing, micro-contact hot printing, step and flash imprint lithography, particle replication in non-wetting templates, and hydrogel templating methods.

Selection of appropriate microfabrication techniques for making microparticles suitable for drug delivery should consider factors including whether it is possible to remove impurities without losing the loaded drug, manufacturing reproducibility, and control of drug release kinetics.

Microparticles can be formulated to contain different mass ratios of polymers to proteins. Typically, the microparticles include a greater mass of polymers than proteins. For example, microparticles can be formulated to include a mass ratio of polymer to protein of between 1:1 and 99:1, e.g., 2:1, 4:1, 9:1, 19:1 and 49:1. In a certain embodiment, microparticles have a 9:1 mass ratio of modified polymer to protein.

The final concentration of therapeutic, prophylactic and diagnostic agents encapsulated within the microparticles can be determined by theoretical mass balance calculations.

In some embodiments, where the encapsulated agent includes botulinum toxin, the microparticles have a mass ratio of polymer to botulinum toxin ranging between 1,000,000:1 and 10:1, inclusive. A preferred method for fabrication of polymer microparticles is by emulsion.

1. Microparticle Fabrication by Emulsion Method

The methods include fabrication of microparticles by emulsion using protein particles obtained by solvent washing of precipitated protein, optionally including dry ball milling in a dry ice chamber, cryomilling, and/or wet ball milling, optionally in a dry ice chamber. For particle formulation by emulsion, protein particles are added to a polymer solution including one or more solvents. Emulsion is typically carried out using a solid/oil/water (S/O/W) emulsion.

In an exemplary method, Zn-precipitated botulinum toxin and albumin proteins are added to a solution of the desired polymer(s) that will be formed into microparticles. The Zn-precipitated protein particles are dispersed in the polymer (e.g., PLGA) dissolved in a selected solvent (e.g., dichloromethane, or mixture of 1:1 dichloromethane:dioxane) to form a solid/oil (S/O) dispersion. The S/O dispersion is then added to an aqueous solution containing poly(vinyl alcohol) (PVA), and zinc ions to prevent the precipitated protein from dissolving in the water.

Typically, proteins formulated into polymer microparticles via emulsion methods are loaded into microparticles with very high efficiency. For example, polymer size and structure can influence loading efficacy from 80%-100%.

a. Selection of Solvents for Emulsion Method

Solvents used in the fabrication of microparticles by emulsion can be selected based upon the desired physical properties, including boiling temperature (BP), and water solubility. Typically, the choice of solvent used for emulsion methods will impact the rate of release of protein drugs encapsulated within the microparticles. A key step in the production of microparticles with controlled release properties is the critical time point at which the organic solvent(s) which the polymer is dissolved in leaves the forming microparticle and the polymer solidifies. Many different interactions occur simultaneously at this interface. One is a solvent-polymer interaction which defines to what degree the polymer prefers to be interacting with the solvent. Another of which is the solvent-drug interaction, which in this case is minimal as the precipitate is largely undissolved in the polymer solvent. A third of which is solvent removal mechanism. Under an emulsion bath, the solvent leaves the forming microparticle and dissolves out into the water. Additionally, the volatile solvent evaporates away from the emulsion as the microparticles form and harden. Similar processes apply to hydrogel template microfabrication approach. In these situations, the rate at which the solvent leaves the polymer matrix is important. If the solvent leaves too quickly, the hardening polymer chains will not have adequate time to reorient together and develop a uniform skin across the microparticle surface. In the absence of this skin, release by diffusion can be very fast as water will quickly enter the microparticle through large pores and dissolve out the loaded therapeutic agent. Since this solvent-removal process is driven by evaporation and dissolution of the solvent into the emulsion bath, the boiling point of the solvent and its water miscibility are key factors to consider. This effect is highlighted in the examples below which detail experiments utilizing varying solvents such as dichloromethane and dioxane. Even when drug and polymer are held constant, the key factors of solvent and other parameters that affect its removal from the microparticles drastically affect the release properties of the drug load.

Exemplary solvents useful for emulsion methods include, but are not limited to, benzyl alcohol (BA), n-butyl acetate (nBA), chloroform (ChF), dichloromethane (DCM), ethyl acetate (EA), ethyl formate (EF), methyl formate (MF), phenethylamine (PhA), triacetin (TAc), and dioxane (Dx). A listing of exemplary solvents and the associated boiling point (BP) and water solubility of each is provided in Table 2, below.

TABLE 2

Solvents useful for emulsion methods.

| Solvents | BP (° C.) | Water solubility (%) |
|---|---|---|
| Benzyl alcohol (BA) | 205 | 3.5 |
| n-Butyl acetate (nBA) | 126 | 0.7 |
| Chloroform (ChF) | 61.2 | 0.8 |
| Dichloromethane (DCM) | 39 | 1.6 |
| Ethyl acetate (EA) | 77.1 | 8.7 |
| Ethyl formate (EF) | 54.7 | 13.6 |
| Methyl formate (MF) | 32 | 3.0 |
| Phenethylamine (PhA) | 194.5 | 3.4 |
| Triacetin (TAc) | 260 | 7.0 |
| Dioxane (Dx) | 101 | 100 |

In some embodiments, a mixture of more than one solvents are used. An exemplary mixture of solvents for use in emulsion formulation of Zn-precipitated botulinum toxin/albumin protein includes combinations of DCM/Dx, BA/EA, BA/MF, ChF/TAc. The protein particles are dispersed in polymer dissolved in a suitable solvent to form "S/O" dispersion, which is then added to a PVA solution containing Zn to keep the precipitated protein from dissolving in water.

b. Emulsion Procedures

Microparticles are produced from solvent-washed protein precipitants dispersed in a desired solvent. Preferably, emulsion methods for fabricating protein/polymer microparticles do not include any steps or reagents that denature, degrade or otherwise irreversibly alter the structure of the protein. Therefore, methods for fabrication of microparticles by emulsion maintains the biological activity of the encapsulated proteins.

In an exemplary method of preparing botulinum toxin/albumin PLGA microparticles, PLGA (750 mg) is dissolved in a suitable volume of a desired organic solvent (e.g., 5 mL of DCM, or DCM/Dx at a ratio of 1:1). A 1% aqueous solution of PVA (31,000 Da) is prepared by dissolving into distilled water. Zinc chloride solution (3 mg/mL) is added to a concentration of approximately 1% (w/v) to form a PVA-Zn solution.

The solvent-washed toxin/albumin precipitate (50 mg) is dispersed into the PLGA solution with vortexing for 10-20 seconds, to make a solid-in-oil (S/O) dispersion. The PVA-Zn solution is homogenized, and the PLGA-botulinum toxin/albumin (S/O) dispersion is added into the PVA-Zn solution.

Addition of the S/O dispersion into the PVA-Zn is carried out using a constant, steady flow rate, for example, 0.25 mL/sec. The mixture is emulsified for a suitable period of time, for example, 1-30 minutes depending on the homogenization speed. An additional 150 mL of PVA-Zn solution is then added into homogenizing emulsion solution and continuously emulsified for 5-30 minutes, preferably 15 minutes. The solution is then quickly poured into 1.6 L of PVA-Zn solution and mixed (e.g., with magnetic stirring at a speed of 600 revolutions/minute; rpm). Mixing of the solution is carried out for a suitable time frame, such as 60-100 minutes, preferably 75 minutes), in a temperature controlled environment to prevent undesirable increases in temperature (e.g., mixing in a 10° C. incubator).

Hardened microparticles are collected using any suitable means, for example, using 75 μm and 20 μm meshes, and are washed with an excess of aqueous solvent (e.g., 3-4 L of distilled water).

The microparticles are collected (e.g., by centrifuged at 5,000 rpm; 4,500 rcf) and can be used immediately or stored in a suitable buffer, or dried (e.g., by freeze-drying overnight) for storage or later use.

Botulinum toxin/albumin microparticles formulated according to the emulsion methods contain toxin that has substantially the same biological activity as prior to being formulated into microparticles. In a particular embodiment, confirmation of the biological activity of solvent-washed toxin used to make PLGA microparticles according to the emulsion method is determined by the FRET assay kit according to standard operating procedure from the suppliers. For example, microparticles are suspended in 5 mL of PBS-Tween (0.05%) (pH 7.5) containing 0.1% sodium azide at 37° C. in a shaking incubator at 50 rpm. At predetermined time points, each test tube is centrifuged, and supernatant is withdrawn for an albumin-release assay, for example, with the microBCA protein assay kit, and for the botulinum toxin ELISA assay with the Tetracore BTX assay kit, and for the toxin enzymatic activity assay with the FRET assay kit according to standard operating procedure from the suppliers. The FRET assay can detect the toxin enzyme activity at the toxin concentration of 1-100 ng/mL. The FRET assay provides an easy and fast way of measuring the enzymatic activity of toxin without the need for lengthy in vivo analyses, such as mouse paralysis experiments.

2. Other Methods for Formulating Microparticles a. Polymer Template Method

Microparticles having a predetermined, homogeneous size have been prepared using a polymer template microfabrication method (Acharya, et al., *J. Control. Release*, 141, pp. 314-319 (2010); Park, et al., Sol-gel phase-reversible hydrogel templates and uses thereof, U.S. Pat. No. 8,951,567 (2015)). In some embodiments, drug-eluting microparticles that enhance the efficacy of encapsulated protein drugs, such as botulinum toxin, are prepared by polymer template microfabrication, also known as the "PVA template method", "hydrogel template method" or "water-soluble polymer mold method" (Acharya, et al., *J. Control. Release*, 141, pp. 314-319 (2010); Park, et al., Sol-gel phase-reversible hydrogel templates and uses thereof, U.S. Pat. No. 8,951,567 (2015); Lu, et al., *Int. J. Pharm.*, 461, pp. 258-269 (2014); He and Park, *Mol. Pharm.*, 13, pp. 2164-2171 (2016)).

A silicon wafer template is prepared with pillars or cavities with a predetermined diameter that can be controlled to any specific value (e.g., from 1.5 μm to 100 μm or larger). Exemplary microparticles of 50 μm are sized suitable for easy injection using common needles for in vivo applications. On top of the silicon wafer template is added a solution of a water-soluble polymer that can form a gel or that can be dried to form a membrane. For example, gelatin is used to form a hydrogel by lowering the temperature; PVA is used to make a tougher, more resilient and easy-to-handle polymer template. The gelatin or PVA template is peeled off the master template and then placed on a flat surface exposing the cavities. The cavities are then filled with drug-PLGA mixture dissolved in organic solvent (e.g., dichloromethane, ethyl acetate or benzyl alcohol). Various PLGA with different molecular weights and different L:G ratios can be used. The main advantage of the hydrogel/polymer template method is in the uniform microparticle size and the easy collection of the microparticles formed in the template. Microparticles are released from the template by simply dissolving the templates in a suitable solvent, such as water.

The released microparticles can be washed and collected by centrifuging or filtering though fine meshes.

i. Protein/Polymer Preparation

Typically, polymer solutions are prepared by dissolving biodegradable polymers into organic solvents. Dry polymer powders for use in the microparticles are weighed at a predetermined concentration (w/v), dissolved into a suitable organic solvent, and the solution is then added directly to the protein precipitate powder. The powder is mixed and homogenized into the polymer solution, for example, by vortexing. In an exemplary method, PLGA, PDLA, PLLA, or PCL are dissolved into organic solvent to bring the solution to approximately 80% of the final volume. Then, the protein powder is added and mixed into the solution and additional organic solvent is added to bring the solution to the final volume.

ii. Template Preparation

The polymer template microfabrication includes the step of template preparation. Typically, templates (e.g., polymer molds) are prepared using a water-soluble polymer, such as PVA, that is used to make polymer molds having microwells of a predetermined size and shape. Exemplary microwells in PVA molds have a diameter of between approximately 500 μm and 1.0 μm, inclusive, for example, sized ranging from 100 μm to 2 μm inclusive, such as 50 μm, 20 μm, or 1.5 μm, with a depth up to 500 μm, for example, 50 μm.

In an exemplary method, the micro-fabrication of microparticles is carried out using a PVA template prepared on a PDMS cast. The method steps for preparation of the PVA template include:

1. Preparation of a 4.0% Solution of PVA;
2. Application of the PVA solution into a PDMS counter mold;
3. Drying of the PVA solution within the PDMS counter mold; and
4. Removal of the PVA template from the PDMS counter mold.

Templates can be formulated to produce microparticles having a range of predetermined sizes and shapes. Exemplary shapes of microparticles include shapes and patterns, such as spheres, cubes, stars, cylinders, etc.

iii. Particle Cup Fabrication

Following preparation of an appropriate template, the polymeric outer shell of "cup" of the microparticle is prepared. Microparticles formulated according to the methods can provide dual or multiple functionalities within a single formulation. For example, multiple release profiles (burst release from outer particles and sustained release from internal components), variability of the kinetics of sustained release, as well as enhanced efficacy of encapsulated proteins relative to conventional delivery systems.

Single Layer Cup Formulations

For preparation of the polymer vehicle or "cup", polymers are poured into the mold and set. Typically, after the PVA mold is prepared, it is secured to a glass plate and 300 µL of polymer-protein mixture solution is layered over the microwells, using a suitable applicator (e.g., a razor blade). The microparticles within the mold are then dried, for example, by overnight exposure to ambient temperature.

Multi-Layer (Onion) Cup Formulations

The methods of particle fabrication can include formation of a polymeric "cup" having more than a single polymer layer (i.e., an "onion cup"). For example, in some embodiments, the fabrication of particles includes step-wise repeats of the process used to prepare a single-layer polymer mold, using the same or different polymer solutions. In an exemplary methods, various PLGA polymers with different L:G ratios, molecular weights, and/or end groups are selected for making microparticles based on the multi-layered (onion) conformation. To make a single-layer cup, a suitable amount (e.g., 100-200 µL) polymer solution is poured on a secured PVA mold to fill the predetermined diameter microwells (e.g., by using a razor blade, while tilting). Subsequently, to add an additional polymer layer to the existing "cup" ("onion cup"; "multi-layer cup"), one or more additional polymer solutions are repeatedly filled in the same way after drying of the previous layer. The multi-layer cups within the PVA mold are then dried, for example, by overnight exposure to ambient temperature.

iv. Filing of Particle Cups

Following formulation of single-layer cups or onion cups, the inner spaces are filled with protein drug powder or crystals, mixed with a suitable polymer solution. In an exemplary method, the relative concentrations of protein drug precipitate and polymer in organic solvent range between are 5-10% (w/v), and 5-20% (w/v), respectively. The solvent is selected considering solubility of the polymer used for fabrication of the single or multi-layer polymer cups. Only those solvents that are compatible with the preformed cup layer (i.e., those that do not dissolve the polymer of a preformed cup layer) can be used.

A suitable amount of polymer solution including protein powder is typically between 100 and 200 µL per template. Incompatible solvents that dissolve the polymer used in fabrication of the cup will compromise the inner surface of the cup layer, potentially producing pores or cracks that can result in an initial burst and low drug loading.

In an exemplary embodiment, the polymer cups are filled with Zn-precipitated botulinum toxin and albumin powder, mixed with 100 and 200 µL polymer solution. After the core of the polymer "cup" is filled, the top cover layer is formed using a "blank" polymer (e.g., PLGA). For the top cover layers, the same polymer as the core is used multiple times, or alternatively, different polymers are used. After formation of the top layer, the PVA molds are dried in at between 20-70° C., for example, by placing within a stationary incubator oven for approximately 3 to 12 hours.

Dried microparticles are collected by dissolving the PVA mold in 10 mL of double distilled water for approximately 30 minutes. The microparticles are then washed and collected by successive filtration through a 106 µm mesh, and through a 38 µm mesh, respectively, using distilled water as a solvent. After removal of residual PVA, microparticles suspended in water are centrifuged at 5,000 rpm (4,500 relative centrifugal force; rcf) for 1~3 min, the supernatant is removed, and microparticles are dried to completion under a vacuum (e.g., overnight at room temperature).

In a particular embodiment, the steps required to fabricate microparticles according to the polymer template method are implemented within an automated machine, such as the SpinSwiper machine (US 2016/0128941 A1 2016). The SpinSwiper machine includes a crossarm which supports a "blade" that feeds solution to a rotating template of microwells present in a PVA template.

E. Agent in Biodegradable Thermogel Polymers and Hydrogels

The methods can include mixing the protein-loaded microparticles or Zn-precipitated proteins into a gel of gel-forming water-soluble polymers. The gel surrounds the microparticles or Zn-precipitated proteins, and provides an additional layer that further controls the release kinetics of the microparticles.

Preferably, the microparticles or Zn-precipitated proteins are mixed with a polymer that is a thermogel. Thermogels exist as a solution and start gelation when the temperature becomes higher than the sol-gel transition temperature. Therefore, polymers dissolved in aqueous solution at room temperature can become a gel upon increases in temperature, for example, to body temperature. Alternatively, the microparticles or precipitates of botulinum toxin/albumin are encapsulated inside hydrogel particles, e.g., crosslinked hyaluronic acid gel particles. The presence of a gel surrounding microparticles presents a diffusion barrier that further controls the kinetics of drug release.

F. Carriers and Excipients

Drug eluting microparticles can be formulated with a pharmaceutically acceptable carrier and/or excipient for administration to tissue or a tissue lumen. Suitable carriers include, but are not limited to, sterile liquids, such as water, saline and phosphate buffered saline, and aqueous or water soluble gels such as polyvinylpyrolidone, polyethylene glycol (PEG), alginate, and hyaluronic acid. Additionally, the carrier may contain thermosensitive polymers. The formulations also can contain minor amounts of wetting or emulsifying agents, or pH buffering agents.

Generally, the microparticles are supplied either separately or mixed together in unit dosage form, for example, as a dry lyophilized powder or water-free concentrate in a hermetically sealed container, such as an ampoule or sachet indicating the quantity of active agent. Where the formulation is to be administered by injection or instillation, it can be dispensed with a syringe, bottle, or other suitable vessel containing sterile pharmaceutical grade water, saline, or other buffer.

Biocompatible microparticles including protein drugs can be formulated into compositions including suitable excipient for administering the microparticles into the body of a subject. In certain embodiments, microparticles including protein drugs are formulated in a carrier or excipient suitable for delivery into a subject by injection, for example, via intramuscular, intravenous, subcutaneous, intraperitoneal, or via skin scarification. Typical carriers are saline, phosphate buffered saline, glucose solutions, and other injectable carriers.

Therefore, formulations including biocompatible microparticles including protein drugs with or without delivery vehicles are described. The biocompatible microparticles can be formulated into pharmaceutical compositions including one or more pharmaceutically acceptable carriers. Pharmaceutical compositions can be formulated for different mechanisms of administration, according to the desired purpose of the biocompatible microparticles and the intended use. Pharmaceutical compositions formulated for administration by parenteral (subcutaneous injection, intramuscular, intraperitoneal, or intravenous), topical or transdermal (either passively or using iontophoresis or electroporation) routes of administration or using bioerodible inserts are described.

Parenteral Administration

In some embodiments, biocompatible microparticles are formulated for administration in an aqueous solution, by parenteral injection. The formulation may also be in the form of a suspension or emulsion. In general, pharmaceutical compositions are provided including effective amounts of an active agent, pharmaceutically acceptable diluents, preservatives, solubilizers, emulsifiers, and/or carriers. Such compositions include the diluents, e.g., sterile water or buffered saline of various buffer content (e.g., Tris-HCl, acetate, phosphate), and optionally additives such as detergents and solubilizing agents (e.g., Tween® 20, Tween® 80 also referred to as polysorbate 20 or 80), anti-oxidants (e.g., ascorbic acid, sodium metabisulfite), and preservatives (e.g., thimerosal, benzyl alcohol) and bulking substances (e.g., lactose, mannitol). Examples of non-aqueous solvents or vehicles are propylene glycol, polyethylene glycol, vegetable oils, such as olive oil and corn oil, and injectable organic esters such as ethyl oleate.

The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

IV. Methods of Use

Incorporation of protein active agents into microparticles and/or thermogels formulated according to the described methods maintains the activity and increases availability of the drug following administration.

The encapsulated protein agents can be released from the microparticles in a continuous or pulsatile manner, according to the design of the particles and composition of the polymer(s) used for fabrication. Upon administration to a subject, such as a human subject, the microparticles provide a controlled-release delivery system that represents an in vivo depot for the active agent. Therefore, the described biocompatible polymer microparticles enable administration of a large quantity of an active agent at a single time. In some embodiments, the delivery of an active agent within biocompatible polymer microparticles enables safe administration of a larger dose of the active agent than would be possible with the active agent alone. For example, when botulinum toxin is loaded into the microparticles, the microparticles provide a system for delivery of botulinum toxin that represents an in vivo depot of botulinum toxin. The depot can release therapeutic amounts of the botulinum toxin from the polymer in a controlled manner that is influenced by the composition of the polymer.

The botulinum toxin can be released from the carrier over of a period of time from about 1 day to more than 3 months, for example, about 6 months.

The microparticle is typically comprised of a substance which is substantially biodegradable, such that the release kinetics of an encapsulated drug from the polymeric particles can be influenced by the rate of degradation in vivo.

A. Methods of Administration

Localized delivery methods have the advantage of reducing severe adverse effects associated with systemic delivery. One advantage to using the described drug eluting microparticles, as opposed to existing formulations for delivery of protein drugs, is that protein drugs in microparticles produced according to the described methods can be more bioavailable, thus delivering smaller amounts of the active agent with the same or greater efficacy.

Formulations of drug eluting microparticles can be administered locally by injection directly into the tissue or instilled into a tissue lumen. Representative tissue lumens include those of the respiratory, gastrointestinal, and urogenital tracts. These include cavities such as the nasal, pulmonary, esophageal, rectal, bladder, vaginal, urethral, and uterine cavities.

In some embodiments the drug eluting microparticles are formulated into a gel which is applied to a target tissue during surgery. In another embodiment, the drug eluting microparticles are suspended in a liquid and injected into a tissue. In a further embodiment, the drug eluting microparticles are instilled into a lumen for an effective amount of time.

The formulations containing drug eluting microparticles can be administered to a desired location in the bladder, other body cavity, or skin by spraying, rolling, painting or sponging a liquid, viscous liquid or gel-like material using a cystoscopy, endoscope, or other suitable scope device. The use of a scope device allows identification of the area of administration before administering the formulation. The scope device can include an applicator for the formulation including, but not limited to, a spraying device, gauze, roller or sponge containing the formulation. The applicator can be protected using a suitable cover until the formulation is to be administered so the formulation is not accidentally applied to an undesired area. The applicator can be attached at the end of the scope device to allow high precision administration. Liquid spray tools for scope devices are known in the art, for example such tool is described in U.S. Pat. Nos. 7,588,172 and 6,354,519 to Yamamoto and Kidooka.

Formulations of drug eluting microparticles can be administered with such regularity to provide effective relief from one or more symptoms of a disease or disorder, prophylactic, diagnostic or cosmetic effects. In some embodiments, the formulations are delivered in a single administration, for example, by a single injection. Typically, the number of administrations of active agent required to achieve a therapeutic or cosmetic effect when delivered within drug eluting microparticles formulated according to the described methods is less than the number of administrations of the same or equivalent active agent required to achieve the same effect in the absence of the microparticles.

B. Dosages

The microparticles can enhance the delivery of protein active agents, such as botulinum toxin, resulting in the sustained effectiveness. See Examples. Therefore, an advantage of using these drug-releasing microparticles for the delivery of protein active agents is the ability to decrease the frequency of administering active agent required to achieve a desired effect, compared with the dosage required when administering formulations of un-encapsulated drugs.

In preferred embodiments, the drug eluting microparticles are administered in an amount effective to achieve relief from one or more symptoms of a disease or disorder, or to achieve a desired cosmetic effect. Preferably, the frequency of administration of active agent required to achieve a therapeutic or cosmetic effect when delivered within drug eluting microparticles formulated according to the described methods is less than that of equivalent active agent administered in the absence of the microparticles.

Different size dosage units of the drug eluting microparticles formulation may be used. A dosage unit containing a dry powder of dehydrated drug eluting microparticles including botulinum toxin and albumin or other protein active agents can be reconstituted in a container with a pharmaceutically acceptable carrier. Preferably, the pharmaceutically acceptable carrier is an aqueous carrier. Suitable amounts of drug-eluting microparticles include, but are not limited to, 0.1-1 mg, 1-10 mg, 10-100 mg, 100-300 mg, 300-600 mg, and 600-1,000 mg.

A dosage form of polymer microparticles loaded with botulinum toxin can include an amount of between about 1 unit and about 50,000 units of the botulinum toxin. Preferably, the quantity of the botulinum toxin associated with the polymer is between about 10 units and about 2,000 units of a botulinum toxin type A. Where the botulinum toxin is botulinum toxin type B, preferably, the quantity of the botulinum toxin associated with the microparticles is between about 100 units and about 30,000 units of a botulinum toxin type B.

Typically, the amount of a type A botulinum toxin administered by the microparticles over a continuous period is between about 0.01 units/kg body weight of the recipient and about 25 units/kg body weight of the recipient, inclusive, preferably between about 0.1 units/kg body weight of the recipient and about 15 units/kg body weight of the recipient, most preferably between about 1 unit/kg body weight of the recipient and about 10 units/kg body weight of the recipient.

Typically, the amount of a type B botulinum toxin administered by the microparticles over a continuous period is between about 0.01 units/kg body weight of the recipient and about 1,000 units/kg body weight of the recipient, inclusive. For example, botulinum toxin can be administered by intramuscular (i.m.) or subdermal (s.d.) injection of polymeric microparticles including botulinum toxin to a muscle of a patient in an amount of between about 1 unit and about 10,000 units.

C. Diseases and Disorders to be Treated

Drug eluting microparticles can be used to deliver protein active agents for treatment of diseases or disorders.

In a preferred embodiment, botulinum toxin is administered to a patient, to treat an affliction such as a movement disorder, including a muscle spasm or bladder disorders, such as overactive bladder, migraines, or wrinkles.

In preferred embodiments, polymer microparticles containing botulinum toxin are used to treat one or more diseases or disorders for which botulinum toxin has been approved for use in the clinic. The amount, regimen, and location of administration can vary according to the disease or disorder to be treated. Therefore, in some embodiments, the dose, the number of injections, the site of injections, and how often the microparticles containing botulinum toxin are administered will be determined by the condition and the response to therapy. Typically, a response (e.g., reduction, cessation or changes in one or more symptoms of the disease or disorder) is observed within 1, 2, 3, 4, 5, 6, or 7 days following administration, or longer, for example up to 2 weeks following administration. The effect of administration can vary according to the disease or disorder to be treated, and can last form one day to one year or longer following administration, for example, for 3 to 6 months following administration.

Typically, polymer microparticles containing botulinum toxin are given by injection, into the affected muscles (e.g., intramuscularly) when treating eye disorders, muscle stiffness/spasms, and wrinkles.

When used to prevent migraines, polymer microparticles containing botulinum toxin are injected into the muscles of the head and neck. Polymer microparticles containing botulinum toxin are injected into the skin (e.g., intradermally) for the treatment of excessive sweating. When treating bladder disorders, such as overactive bladder, polymer microparticles containing botulinum toxin are injected into the muscles or lumen of the bladder.

Improved efficacy in treatment of bladder disorders is obtained using biocompatible polymer microparticles for administration of botulinum toxin or other protein active agents. The microparticles are typically administered in a pharmaceutically acceptable carrier, such as saline or phosphate buffered saline by injection or instillation into the tissue or lumen of the bladder.

Representative bladder disorders that can be treated with the formulations include, but are not limited to, hemorrhagic cystitis, interstitial cystitis/painful bladder syndrome (IC/PBS), and cancer. Symptoms that can be alleviated by treatment with botulinum toxin encapsulated within drug eluting microparticles include, but are not limited to, hematuria, urinary urgency, supra pubic pain, inflammation, and urinary retention.

Botulinum toxin relaxes muscle by blocking the release of a chemical called acetylcholine. Therefore, in some embodiments, botulinum toxin (e.g., toxin type A and B) encapsulated within polymer microparticles is used to treat disorders associated movement, such as with muscular activity relating to movement of the eye, muscle stiffness/spasms, etc.

In some embodiments botulinum toxin encapsulated within polymer microparticles is used to treat crossed eyes (strabismus) or uncontrolled blinking (blepharospasm), to treat muscle stiffness/spasms or movement disorders (such as cervical dystonia, torticollis).

The formulations can also be used to treat disorders of other parts of the body including, but not limited to, the vagina, gastro-intestinal tract (upper and lower), mouth, airway, esophagus, nasal cavity, ear canal, and skin.

It is also used to treat severe underarm sweating. Botulinum toxin works by blocking the chemicals that turn on the sweat glands. In some embodiments, botulinum toxin encapsulated within polymer microparticles to reduce the cosmetic appearance of wrinkles. It is also used to prevent headaches in people with very frequent migraines.

The present invention will be further understood by reference to the following non-limiting examples.

EXAMPLES

The following examples illustrate the biodegradable polymer formulations for sustained release in vitro and in vivo efficacy of toxin as measured by the mouse paralysis test. The "Mouse Unit" described in the examples varies slightly, because the efficacy of toxin in different lots needed to be measured using only a limited number of mice. Thus, in each example, the solution control formulation was always used to compare the efficacy of biodegradable polymer formulations.

Example 1: Formulation of Drug-Eluting Biodegradable Polymer Microparticles Having Various Properties Materials and Methods Formulation of Botulinum Toxin/Albumin Microparticles Type A complex from *Clostridium botulinum* available from List Biological Laboratories, Inc. (Campbell, Calif.).

Botulinum toxin (100 μg) was diluted with 1 mL of Tris buffer. The solution was made into 100 μL aliquots and frozen. Each 100 μL aliquot (containing 10 μg toxin, or approximately 10,000 Mouse Units) was diluted in 20 mL albumin solution (50 mg/mL in 50 mM Tris-HCl pH 7.5).

The series of steps commonly involved in incorporating proteins into biodegradable polymer microparticles often denatures the proteins, resulting in a loss or reduction in their bioactivity P. A. Schellman, Solvent denaturation, Biopolymers, 17 (1978) 1305-1322; M. van de Weert, W. E. Hennink, W. Jiskoot, Protein instability in poly(lactic-co-glycolic acid) microparticles, Pharm. Res., 17 (2000) 1159-1167].

The botulinum toxin was mixed with serum albumin (toxin/albumin), and precipitated using zinc chloride. The toxin/albumin precipitate obtained by zinc chloride is referred to as Zn-precipitated toxin or Zn-precipitated proteins.

Proteins started to precipitate at zinc chloride concentrations of about 0.1%. Albumin assay showed that more than 99% of albumin was precipitated by zinc chloride. Usually the final zinc chloride of 1% was used. The solution was centrifuged to collect the Zn-precipitated proteins by removing the supernatant and freeze dried. Zn-precipitated toxin maintained its bioactivity, as measured by the mouse paralysis test and in vitro toxin endopeptidase activity using SNAP-25 substrate, even after going through various steps in making biodegradable polymer microparticles.

Fluorescence resonance energy transfer (FRET) SNAP-25 endopeptidase assay kit (Biosentinel's Botest) was used to measure the ability of toxin to cleave proteolytically the natural SNAP-25 substrates. The FRET assay allowed for detection of toxin activity without using the mouse paralysis study, allowing testing of many toxin formulations.

Alternatively, after the supernatant was removed, the remaining Zn-precipitated proteins were washed with a selected solvent (solvent washing) for further processing, as described. The solvent washing step was critical for preparation of toxin-loaded microparticles by our new emulsion method.

In Vitro Drug Loading and Release Tests

The amount of botulinum toxin required as a single dose for clinical use in humans is very small (e.g., nanogram (ng) quantities are required). Typically, the amount of botulinum toxin required to be incorporated into microparticles is far smaller than the amount of albumin incorporated into the same particles. Therefore, values for protein release studies were determined by measuring the albumin release kinetics.

The microparticles were weighed after drying and separated into several samples of less than 10 mg for studying albumin release, drug loading, and morphology analysis, respectively. Drug loading was determined by dissolving a sample in 1 mL of dioxane. The sample was centrifuged, the supernatant was removed, and remaining Zn-precipitate was dissolved in 1 mL of 0.05 M NaOH. Alternatively, the polymer microparticles are dissolved in dioxane/acetonitrile mixture and the protein precipitate is dissolved in 0.1 M NaOH. By either method, the protein is tested by the bicinchoninic acid (BCA) assay (Thermo Scientific prod #23225).

For long-term albumin release, triplicate samples of dried microparticles were incubated at 37° C. in 1 mL of 0.01 M phosphate buffered saline with 0.05% Tween® 20 (PBST) at pH 7.4 containing 0.1% sodium azide. At predetermined time points, samples were vortexed for 10 seconds, centrifuged at 7,200 rpm for 2 minutes and the supernatant was taken for analysis. Albumin content was analyzed by the BCA assay and cumulative release was recorded.

In Vitro Accelerated Degradation Tests

Microparticles were incubated at 60° C. in 1 mL of 0.1 M sodium acetate buffer at pH 3.0. A sample of microparticles from each formulation was observed by light microscopy at specified time points. Changes in shape or size of microparticles were noted to determine the degradation time.

Typically, the amount of botulinum toxin used clinically is in the range of 100 units or less. The amount of toxin used was in the range of 100 ng, making it very difficult to handle, if it is not diluted with other proteins, such as albumin. The addition of approximately 1 mg of serum albumin for each unit of toxin provides a ratio of toxin to albumin of about 1:10,000, without impacting the activity or release kinetics of the botulinum toxin. Thus, to determine the impact of different polymer microparticle formulations on the kinetics of protein release, microparticles were loaded with albumin alone.

Results

Microparticles were designed to deliver albumin such that the first 40-50% of the total dose is released within a few days following parenteral administration, and the remaining dose is released slowly over a period of time ranging from weeks to months.

Since the protein release kinetics depends upon the type of PLGA used, including (1) average molecular weight of the polymer; (2) L:G ratio; and (3) incorporation of either ester or acid end groups, various types of polymers were used to make microparticles and examined their albumin release behavior, including poly(lactic acid) (PLA), poly(D-lactic acid) (PDLA), poly(L-lactic acid) (PLLA), poly(lactic-co-glycolic acid) (PLGA), and polycaprolactone (PCL).

Albumin was loaded into biodegradable polymer microparticles after solvent washing of Zn-precipitated protein. Biodegradable polymers of various molecular weights and L:G ratios were used to make 50 μm microparticles. The biodegradable polymer concentration was varied from less than 10% to more than 40%. The albumin concentration ranged from less than 5% to more than 20% of the total weight. Solvents used to dissolve biodegradable polymers include dichloromethane, dioxane, ethyl acetate, and benzyl alcohol. The release profiles of the initial 78 biodegradable polymer formulations are shown in FIG. 1. As shown in FIG. 1, the release profiles vary greatly depending on the composition and method used to make microparticles.

Several general observations were made on the albumin release profiles:

1. PLLA formulations have the advantage over PDLA formulations for minimizing the initial burst release of bovine serum albumin (BSA) in the molecular weight range of 20,000~250,000 Da. This may be due to the high degree of crystallinity of poly(L-lactic acid) (PLLA) and the relative low crystallinity of poly(D-lactic acid) (PDLA). The high degree of crystallinity allows even the BSA near the surface to be trapped and minimizes burst release;

2. Microparticles made of mixtures of PDLA and PLLA showed hybrid release profiles, i.e., the initial burst release was between those obtained by individual polymer formulations, followed by the steady state release;

3. The microparticle formulation made of a 50:50 physical mixture of PLLA and PDLA showed near zero-order release for over 5 months with only 12% initial burst release; and 4. The type of solvent used affected the extent of the initial burst release. The burst release was higher for the dichloromethane (DCM) formulations than the dioxane formulations. The boiling points of DCM and dioxane are 39° C. and 101° C., respectively, and the faster drying of DCM might have resulted in less compact polymer structures, for a higher initial burst release.

Having the ability to control the release profiles of PLGA formulations is one of the most important factors in developing long-term dosage forms. The ability to control the initial burst release, steady-state release, and degradation time allow for the development of delivery systems for countless applications from near zero order release to multiple pulsatile releases delivered over a period of time.

The data in FIG. 1 show that the release profiles are greatly influenced by polymer crystallinity (controlled by polymer type), polymer molecular weight, L:G ratio of the polymer, microparticle shape, and solvent. These microparticles were formulated using the hydrogel template method.

Example 2: Polymer Microparticles Increase the Amount of Botulinum Toxin that can be Safely Administered Methods Formulation of Botulinum Toxin/Albumin-Loaded Polymer Microparticles Botulinum toxin and albumin in aqueous solution were precipitated using various precipitating agents, including salts, carbon fatty acids, PEG, solvents, amino acids, and zinc chloride ($ZnCl_2$). Of these, $ZnCl_2$ was chosen for its ability to precipitate both proteins and for easy handling of the precipitated proteins. At the $ZnCl_2$ concentration of 1% (or 73 mM), 99% of the protein in solution precipitated. The precipitated proteins were collected by centrifuge and freeze-dried.

The toxin/albumin powder was manually ground using a pestle and mortar, and varying toxin amounts were loaded into biodegradable polymer microparticles. For the albumin release and other kinetic studies, a wide variety of polymers including PLGA, PLLA, PDLLA, and PCL were used. Simply, due to its history of clinical usage, PLGA was utilized for the toxin studies.

The Mouse Paralysis Model.

The potency of botulinum toxin for therapeutic treatment is measured by the mouse unit. One mouse unit of botulinum toxin A is defined as the amount that is lethal to 50% ($LD_{50}$) of a group of a certain weight, strain, and sex of mice (e.g., 18-20 g female Swiss-Webster mice).

To examine the efficacy of released toxin in vivo without killing mice, the mouse paralysis model was used. Biodegradable polymer microparticles or gel formulations were injected to mice intramuscularly using a 25~27-gauge needle attached to the 1 mL syringes. Although the mouse unit is well defined, the potency may vary depending on the preparation of toxin and also the group of mice used. In these studies, most mice died if injected with more than 0.75 unit of toxin in solution. On the other hand, mice exhibited paralysis when the administered toxin ranged between 0.50 and 0.75 units. Thus, there was a narrow window of toxin dose that could be used to study the toxin potency using the mouse paralysis model. The mouse paralysis is analyzed using the digit abduction score (DAS) assay, and the DAS response ranges from 1 to 4 (Aoki, *European Journal of Neurology*, 6, S3-S10 (1999), Aoki, K. R. "A comparison of the safety margins of botulinum neurotoxin serotypes A, B, and F in mice." Toxicon 39.12 (2001): 1815-1820). The high DAS response indicates the stronger paralysis. The paralysis after toxin injection, either in solution or polymer formulation, was used as a measure of the toxin efficacy.

The dose of toxin is described by reference to the "Mouse Unit", where 1 mouse unit is equal to approximately 1 ng, but can range to as little as 50 pg. The exact amount of biologically-active toxin per unit can vary and is batch dependent.

Results

Figure 2:
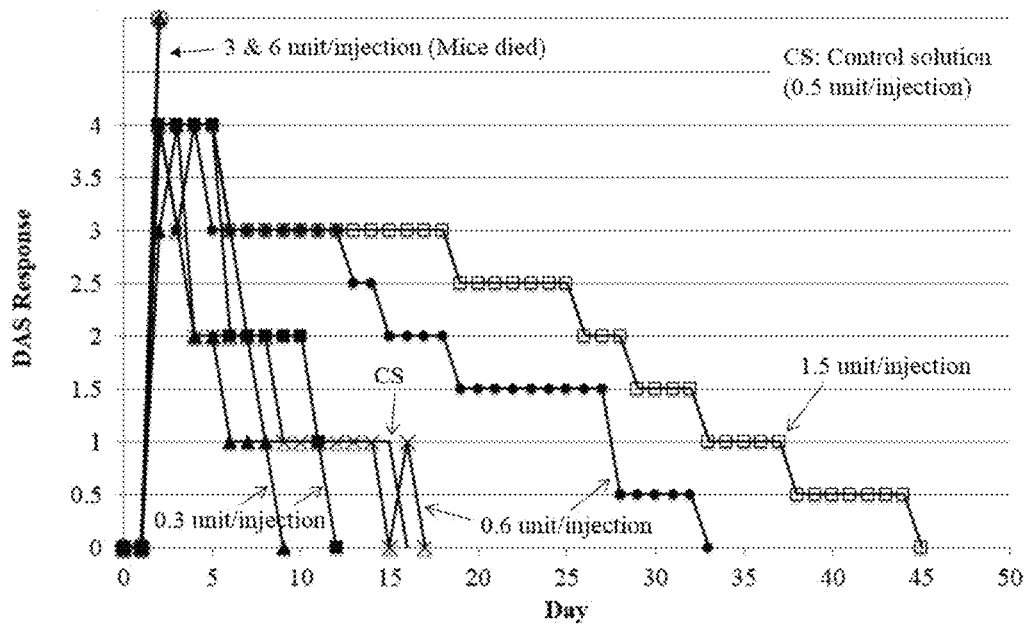
FIG. 2 is a line graph showing digit abduction score (DAS) assay responses (0-4) over time (days) following injection of botulinum toxin delivered in aqueous solution (Control; (−)) and in PLGA microparticles containing 0.3 (▲, ■), 0.6 (x, ●), 1.5 (□), 3 (Δ), and 6 (○) units/injection, respectively. PLGA used was L:G=75:25, 107,000 Da, and 15% (w/v) dissolved in dichloromethane (DCM).

Botulinum toxin/albumin was loaded into biodegradable polymer microparticles after manual grinding. FIG. 2 shows the results of the extent of paralysis after injection of microparticles containing different toxin units.

All mice injected with the total toxin dose of 3 units and 6 units died, because more than 1 unit was released in the beginning. When the total toxin in the microparticle was 1.5 units (which kills mice if injected as solution), the paralysis in the mice was maintained for 45 days.

In another group, control mice injected with 0.5 unit toxin solution showed paralysis only for 16 days. In this group of mice, injecting 0.75 unit solution toxin killed mice, and therefore a total does of only 0.5 unit toxin in solution was injected. On the other hand, even though the microparticles delivered a total dose of 1.5 unit toxin, mice did not die. In contrast, the mice became paralyzed for much longer than mice injected with 0.5 units of toxin in solution.

These data demonstrate the microparticle toxin delivery system provides a safe means for extending the effects of a single administration of botulinum toxin.

Example 3: Polymer Microparticles Increase the Efficacy of Botulinum Toxin

Botulinum toxin/albumin-loaded polymer microparticles were prepared as described in Example 2. The control 0.5 units solution maintained the mouse paralysis for about 16 days, while microparticle formulations extended the toxin effect up to 37 days, depending on the toxin amount loaded into the microparticles.

Figure 3:
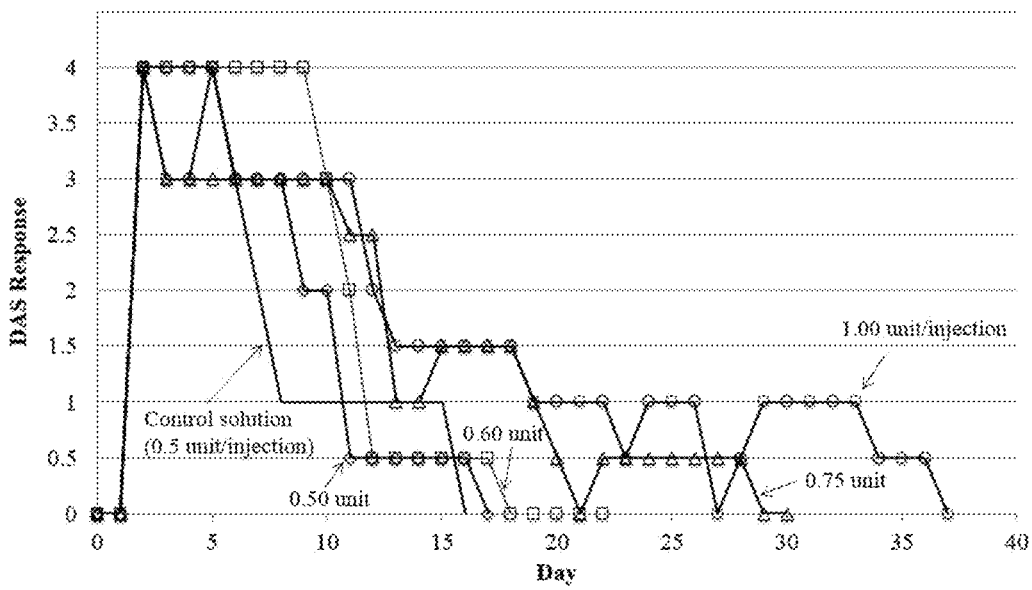
FIG. 3 is a line graph showing digit abduction score (DAS) assay responses (0-4) over time (days) following injection of botulinum toxin delivered in aqueous solution (Control; (−)) and in PLGA microparticles containing 0.5 (◊), 0.6 (□), 0.75 (Δ), and 1 (○) unit/injection, respectively. PLGA used was L:G=75:25, 107,000 Da, and 15% (w/v) dissolved in dichloromethane (DCM). PLGA used for 0.75 and 0.50 units was L:G=60:40 and 120,000 Da, and PLGA for 1 and 0.6 units was L:G=85:15 and 150,000 Da.

As shown in FIG. 3, the long-term efficacy of toxin by a microparticle formulation depends on the toxin amount injected into mice. The Mouse Paralysis study of low dose toxin-loaded biodegradable polymer microparticles demonstrated that the amount of toxin used in microparticles is proportional to the length of time for which the effects of the toxin. If the amount of toxin exceeds 0.75-1.00 unit in solution, the mice die. In contrast, if the same amount is delivered using microparticles, the toxin effect lasts longer without killing mice.

Example 4: Polymer Microparticles in Thermogels Increase the Efficacy of Botulinum Toxin Methods Zn-precipitated toxin/albumin particles prepared by the emulsion method were dispersed in a thermogel to test the efficacy of Zn-precipitated toxin and subsequent solvent washing. In addition, the effect of thermogels on extending the toxin efficacy was also examined.

Thermogels including PLGA-PEG-PLGA triblock copolymers that dissolve in aqueous solution at low temperature (e.g., 4° C.) became a gel at body temperature. The gelling temperature depends on the chemical structure and molecular weight of a thermogel. Because of the presence of a gel surrounding microparticles, the toxin release was further controlled. The Zn-precipitates without thermogels were used as controls. The thermogel was dissolved in distilled water and zinc chloride solution (3 mg/mL) at the 20% (w/v) concentration at 4° C.

Toxin thermogel mixtures (50 μL) were injected to mice intramuscularly using a 25~27-gauge needle attached to the 1 mL syringes.

Results

Figure 4:
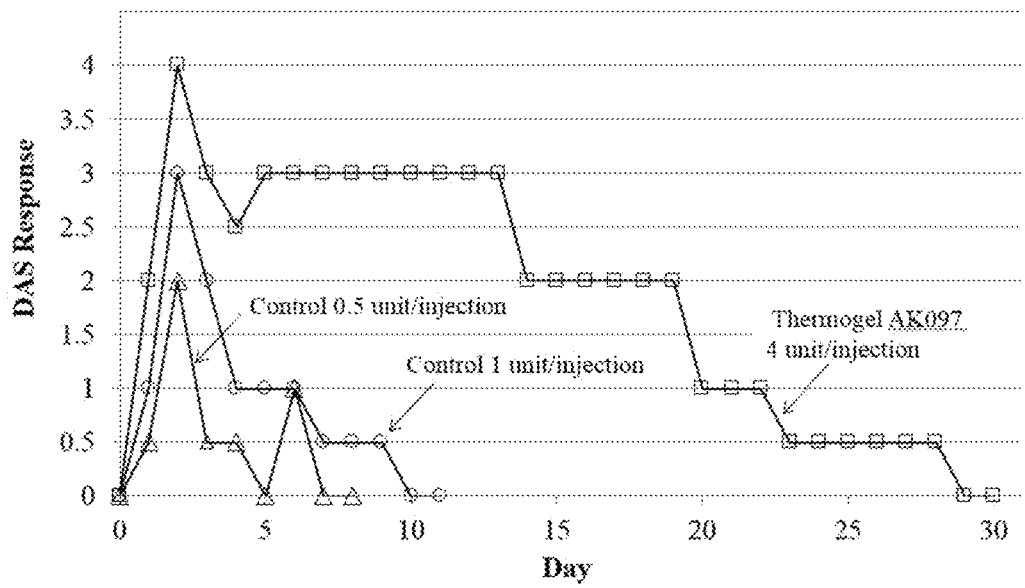
FIG. 4 is a line graph showing digit abduction score (DAS) assay responses (0-4) over time (days) following injection of Zn-precipitated botulinum toxin/albumin delivered in aqueous solution (Control; (Δ/○)) and in PLGA microparticles dispersed in a thermogel (AK097 from Akina PolySciTech) containing 4 units/injection (□). AK097 is a triblock copolymer of PLGA and poly(ethylene glycol) (PEG), PLGA-PEG-PLGA triblock copolymer with the weight average molecular weight ($M_w$) of 6,300 Da. PLGA microparticles were made of 3 outer layers of PLGA 50:50, 44,000 Da, 7% (w/v) filled with toxin/albumin (5%) in PLGA 85:15, 24,000 Da, 5% (w/v) and covered with PLGA 85:15, 24,000 Da, 20% (w/v).

As shown in FIG. 4, the formulation containing 4 units of toxin did not kill mice, but showed stronger DAS responses with much longer-lasting efficacy. The wet-milled toxin maintained its efficacy, as did manually ground toxin. In other studies, microparticles containing 3 units of toxin killed mice, when the microparticles were injected without the thermogel. The area under the curve, i.e., the DAS response as a function of time, for the microparticle/thermogel formulation was approximately 4 times higher than the 1 unit control. The toxin efficacy is related to the total unit delivered. As shown in FIG. 1, microparticles made of different types of biodegradable polymers can release the loaded albumin (and thus, toxin also) with various release kinetics, and the toxin effect can be extended even further than shown in FIGS. 2-4 with higher toxin amounts.

Example 5: Thermogels Extend the Efficacy of Zn-Precipitated Botulinum Toxin Methods To examine the effect of different types of thermogel in controlling and sustaining toxin release, Zn-precipitated toxin was dispersed in zinc solution at 3 mg/mL in distilled water along with a thermogel. Two different types of thermogels were used delivering 2 or 3 units of toxin.

Results

Figure 5:
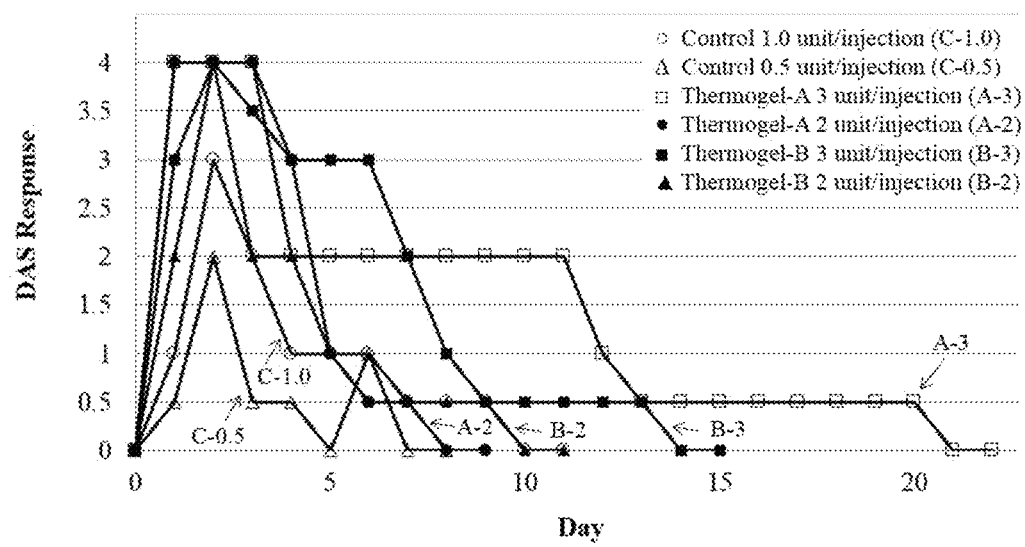
FIG. 5 is a line graph showing digit abduction score (DAS) assay responses (0-4) over time (days) following injection of Zn-precipitated botulinum toxin/albumin delivered in aqueous solution having 1 unit and 0.5 units, respectively (Control; (Δ/○)), and Zn-precipitated toxin/albumin in Thermogel A containing 2 (●) and 3 (□) units/injection, and Thermogel B containing 2 (▲) and 3 (■) units/injection, respectively. Thermogels A and B are AK 019 and AK091 PLGA-PEG-PLGA triblock copolymers having the same $M_w$ of 6,400 Da but thermo-gelling temperatures of 27.5° C. and 30.0° C., respectively.

As shown in FIG. 5, thermogel formulations containing 2 or 3 units of toxin in general extended the toxin efficacy without killing mice. These findings indicated that thermogels provide the ability to retard the release of toxin. Various thermogels were tested to examine their ability to sustain the efficacy of Zn-precipitated toxin dispersed in thermogels. The thermogels used include PLGA-PEG-PLGA triblock copolymers and other type of block copolymers available from Akina PolySciTech (West Lafayette, Ind.). Table 3 lists thermogels tested. Thermogels become gels above the sol-gel transition temperature. Zn-precipitated toxin/albumin particles were mixed with thermogels and injected into mice.

TABLE 3

Thermogels obtained from PolySciTech used for sustained delivery of toxin.

| Thermogel Polymers (PLGA-Based) | L:G Ratio (W/W) | Mol. Wt. (Da) | Gel Morphology |
| --- | --- | --- | --- |
| PLGA-PEG-PLGA (AK012) | 50:50 | 1,000-1,000-1,000 | Transparent |
| PLGA-PEG-PLGA (AK019) | 50:50 | 1,500-1,500-1,500 | Transparent |
| PLGA-PEG-PLGA (AK024) | 75:25 | 1,100-1,000-1,100 | Transparent |
| PLGA-PEG-PLGA (AK085) | 50:50 | 1,400-1,500-1,400 | Transparent |
| PLLGA-PEG-PLLGA (AK087) | 75:25 | 1,100-1,000-1,100 | Opaque |
| PLGA-PEG-PLGA (AK091) | 86:14 | 1,500-1,500-1,500 | Transparent |
| PLGA-PEG-PLGA (AK097) | 94:06 | 1,700-1,500-1,000 | Transparent |
| PDLL-PEG-PDLL (AK100) | 100:0 | 1,700-1,500-1,700 | Transparent |
| PDLL-PEG-PDLL (AK046) | 100:0 | 1,000-1,000-1,000 | Transparent |

| Thermogel Polymers (Caprolactone-Based) | CL:LA Ratio (W/W) | Mol. Wt. (Da) | Gel Morphology |
| --- | --- | --- | --- |
| PLCL-PEG-PLCL (AK108) | 75:25 | 1,600-1,500-1,600 | Opaque |
| PLCL-PEG-PLCL (AK109) | 60:40 | 1,700-1,500-1,700 | Opaque |
| mPEG-PCL (AK036) | 100:0 | 750-2,500 | Opaque |
| PCL-PEG-PCL (AK035) | 100:0 | 1,000-1,000-1,000 | Opaque |

PDLL: poly(DL-lactide); P(LCL): Poly(lactide-co-caprolactone); mPEG: methoxy PEG; PCL: polycaprolactone; PLLGA-PEG-PLLGA: L-chiral lactide in PLGA-PEG-PLGA otherwise is DL racemic.

The results of mouse paralysis by various thermogel formulations are summarized in Table 4. These data demonstrate that some thermogels were effective, while others were not. If the sol-gel transition temperature is too low, i.e., at room temperature of lower, then the solution starts to form a gel even during the injection into mouse. The faster gel formation may be advantageous for many applications, however in some instances gel formation occurred during injection, resulting in administration of less than the desired quantity of toxin to the mouse. In summary, thermogels having a sol-gel transition temperature of approximately 37° C. resulted in higher efficacy than the control.

TABLE 4

Mouse paralysis by Zn-precipitated toxin/albumin in thermogel formulations.

| Toxin-Thermogel Formulation (in 3 mg/mL of zinc solution) | Paralysis days | Observations |
| --- | --- | --- |
| Control solution (<1 unit) | 9-18 days | |
| PLGA-PEG-PLGA (AK012) (1 unit) | 11 days | Too low sol-gel temperature. Gel was formed during injection. |
| PLGA-PEG-PLGA (AK019) (3 units) | 20 days | |
| PLGA-PEG-PLGA (AK024) (2 units) | NA | Mixed with another thermogel |
| PLGA-PEG-PLGA (AK085) (2 units) | 11 days | |
| PLGA-PEG-PLGA (AK091) (2 units) | 13 days | |
| PLGA-PEG-PLGA (AK097) (2 units) | 26 days | |
| PDLL-PEG-PDLL (AK100) (2 units) | 20-21 days | |

TABLE 4-continued

Mouse paralysis by Zn-precipitated toxin/albumin in thermogel formulations.

| Toxin-Thermogel Formulation (in 3 mg/mL of zinc solution) | Paralysis days | Observations |
|---|---|---|
| P(L-co-CL)-PEG- P(L-co-CL) (AK108) (2 units) | 24-30 days | |
| PDLL-PEG-PDLL (AK046) (2 units) | | Mixed with another thermogel |
| AK012 + AK046 (2 units) | 25 days | Sol-gel temperature of 37° C. |
| AK012 + AK085 (2 units) | 26 days | Sol-gel temperature of 37° C. |
| AK024 + AK085 (2 units) | 19 days | |

PDLL: poly(DL-lactide), P(L-co-CL): Poly(lactide-co-caprolactone), mPEG: methoxy PEG, PCL: polycaprolactone

Example 6: The Size of Zn-precipitated Toxin/Albumin Precipitates Influences Efficacy Freeze-dried Zn-precipitated toxin/albumin powdered particles were ground to smaller particles, having dimensions in the range of micrometer and sub-micrometer sizes.

Methods

Particles of freeze-dried Zn-precipitated toxin/albumin were ground manually (i.e., by hand using a pestle and mortar), or using a planetary ball mill machine (Changsha Deco Equipment Co., China) using grinding balls made of zirconium oxide, stainless steel, agate, tungsten, alumina or variable plastics such as Teflon with steel core.

For wet milling, freeze-dried toxin/albumin particles were suspended in an organic solvent of dichloromethane (DCM) or n-butyl acetate (nBA). Wet milling processes were carried out in the absence or presence of dry ice.

Results

The freeze-dried Zn-toxin/albumin precipitate was ground manually for periods of time up to several hours to produce an average particle size of approximately 10 μm.

Average particle size was reduced by a factor of 10 (i.e., to a size of approximately 1 μm or less) when ground by planetary ball milling (which is called dry milling or dry grinding). The dry grinding process resulted in significantly reduced toxin, bioactivity, however, as shown by a reduced paralysis in test animals, likely due to increase in temperature of eth sample caused by the dry milling process.

To prevent temperature increases during the dry milling process, the milling chamber was surrounded by a chamber filled with dry ice in planetary milling machine and the milling process was continued for 2 hours. The chamber was filled with fresh dry ice after 1 hour.

The freeze-dried Zn-precipitated toxin/albumin particles prepared by dry milling with temperature controlled by the dry ice chamber exhibited preserved toxin bioactivity, demonstrating that temperature increases during dry milling is negatively effects toxin efficacy.

The temperature increase during milling was also obviated by milling the freeze-dried Zn-precipitated toxin/albumin particles in the presence of an organic solvent. This process is called wet milling or wet grinding.

Both of the hand ground and planetary ball milled toxin samples were used to make microparticles. The results of mouse paralysis assay in Table 5 show that toxin activity was maintained during dry grinding process if the dry ice chamber was used and during the wet grinding process with and without the dry ice chamber.

TABLE 5

Mouse assay results of freeze dried toxin/albumin particles after milling.

| Grinding Method | Solvent | Mouse lethality (7-10 unit/injection) | Size after process |
|---|---|---|---|
| Hand grinding | | Dead | 5-10 μm |
| Dry mill without dry ice | | Survival (Partial activity) | <2-5 μm |
| Dry mill with dry ice | | Dead | <2-5 μm |
| Wet mill without dry ice | n-Butyl acetate | Dead | <2-5 μm |
| Wet mill with dry ice | n-Butyl acetate | Dead | <2-5 μm |

To confirm that exposure of freeze-dried Zn-precipitated toxin/albumin particles to organic solvents did not impact the biological activity of botulinum toxin, Zn-precipitated toxin particles were mixed with organic solvents, and the toxin activity in vivo was assessed following injection into test animals. As shown in Table 6, the bioactivity of toxin was maintained after being exposed to n-butyl acetate, dioxane or dichloromethane. These solvents are commonly used in making PLGA microparticles, therefore freeze-dried Zn-precipitated toxin/albumin particles prepared by dry and/or wet milling can be mixed with PLGA-dissolved solvents for formulating into microparticles according to polymer template methods, or emulsion methods.

TABLE 6

Toxicity test results of the freeze-dried Zn-precipitated toxin/albumin particles after exposing solvents.

| | Solvent | Mouse lethality (10 unit/injection) |
|---|---|---|
| Control freeze-dried particles | | Dead |
| Freeze-dried particles after exposing solvent | n-Butyl acetate | Dead |
| | Dioxane | Dead |
| | Dichloromethane | Dead |

Example 7: Washing of Zn-Precipitated Toxin/Albumin in Aqueous Solution with Organic Solvents Methods Zn-precipitated botulinum toxin/albumin powder was dispersed in aqueous solution and washed with water miscible solvents to remove water from the precipitate and disperse it in polymer-dissolved solutions to formulate microparticles. The toxin/albumin precipitate in aqueous solution was collected by centrifugation (5,000 rcf, 2 mins.). The supernatant (water) was removed, and a water-miscible solvent was added into the precipitate at a volume ratio of 10:1 (solvent:precipitate), or higher, and mixed by vortexing or stirring to produce a solvent-washed toxin/albumin solution.

A total of 21 different wash solvents were compared for their ability to preserve the efficacy of botulinum toxin encapsulated in microparticles. A list of the solvents assessed for the step of solvent washing is provided in Table 7. For each test solvent, the solvent-washed toxin/albumin precipitate was collected by centrifugation (5,000 rcf, 2 mins.). The collected precipitate was diluted by addition of a solution containing 3 mg/mL zinc chloride, to yield a solution containing approximately 10 units of botulinum toxin. To assess the effect of each of the wash solvents upon botulinum toxin activity, test samples of approximately 50

µL of each solvent-washed botulinum toxin solution was injected into test animals via the intramuscular (IM) route.

Results

Table 7 lists the solvents used to identify those that maintain toxin activity after solvent washing. Solvents listed as Nos. 1-14 maintained toxin activity after solvent washing, as demonstrated by maintained lethality within 48 hours following injection in mice. Solvents listed as Nos. 15-21 did not maintain toxin activity, as demonstrated by survival of mice 48 hours following injection. Of note, although solvents #11-14 maintained toxin activity, these solvents exhibit relatively high viscosity, preventing the ready collection of the solvent-washed precipitate by centrifugation.

Table 6 also provides the results of the paralysis study, which was carried out using approximately 2 units/injection. In this assay, DAS response between 2 and 4 indicated botulinum toxin having biological activity. Solvents Nos. #1-5 and 9 showed similar efficacy as control precipitate that was not washed with solvent. In particular, solvent Nos. 1-3, (i.e., acetone, acetonitrile, and dioxane), were identified as good candidates for washing toxin/albumin precipitates for making PLGA microparticles because these dissolve PLGA, while the other solvents (Nos. 4-21) tested do not.

TABLE 7

Solvents used for solvent washing, and mouse lethality and paralysis data.

| No. | Solvent | Mouse lethality within 48 hours (10 unit/injection) | DAS # at Day 10 (2 unit/injection) | Viscosity (mPa · s) |
|---|---|---|---|---|
|  | Control precipitate | Dead | 3 |  |
| 1 | Acetone | Dead | 4 | 0.30 |
| 2 | Acetonitrile | Dead | 3 | 0.33 |
| 3 | Dioxane | Dead | 4 | 1.37 |
| 4 | Ethanol | Dead | Dead | 0.98 |
| 5 | 2-Methoxy ethyl acetate | Dead | 2 | 1.06 |
| 6 | Methoxy ethanol | Dead | 0 | 1.72 |
| 7 | Ethoxy ethanol | Dead | 0.5 | 2.50 |
| 8 | Butoxy ethanol | Dead | 0 | 2.90 |
| 9 | 2-Propanol | Dead | 4 | 2.04 |
| 10 | Propylene glycol methyl ether | Dead | 0 | 1.70 |
| 11 | Ethanediol | Dead |  | 16.10 |
| 12 | 1,2-Propanediol | Dead |  | 40.40 |
| 13 | tert-Butyl alcohol | Dead |  | 5.88 |
| 14 | Diethylene glycol | Dead |  | 35.70 |
| 15 | Methanol | Survival |  | 0.50 |
| 16 | N-methylpyrrolidone | Survival |  | 1.65 |
| 17 | Dimethylacetamide | Survival |  | 0.94 |
| 18 | DMF | Survival |  | 0.92 |
| 19 | Dimethylsulfoxide | Survival |  | 1.99 |
| 20 | Pyridine | Survival |  | 0.95 |
| 21 | Tetrahydrofuran | Survival |  | 0.46 |

Based on the solvent assessment test, solvent-washed toxin/albumin precipitate was mixed with PLGA dissolved in dioxane, DCM, n-butyl acetate, and other solvents for making PLGA microparticles.

Example 8: Emulsion Methods for PLGA Microparticles Loaded with Solvent-Washed Toxin Methods Particle Formulation PLGA (750 mg) was dissolved in 5 mL of solvent (DCM or DCM/Dx=1:1) and stored in refrigerator (4~10° C.). PVA having a molecular weight of 31,000 Da was dissolved in distilled water and zinc chloride solution (3 mg/mL) at a concentration of 1% (w/v) ("PVA-Zn"). Solvent-washed toxin/albumin precipitate (50 mg) was dispersed in the PLGA solution with vortexing for 10-20 seconds, to make a solid-in-oil (S/O) dispersion. The PVA-Zn solution (250 mL in 400 mL vessel) was homogenized using an L5M-A lab mixer (Silverson Machines, Inc.) with square holes high shear screen type of rotor at 4,000 rpm for 1 minute in an ice bath.

The S/O dispersion was added into the PVA-Zn solution using a 5 mL pipet at a flow rate of 0.25 mL/sec and then emulsified for 15 minutes. The 150 mL of PVA-Zn solution was added into homogenizing emulsion solution and continuously emulsified for additional 15 minutes. The solution was then quickly poured into the 1.6 L of PVA-Zn solution with magnetic stirring at 600 rpm. Stirring was continued for 75 minutes in a 10° C. incubator. The hardened microparticles were collected with 75 µm and 20 µm meshes and were subsequently washed with 3-4 L of distilled water. The microparticles were centrifuged at 5,000 rpm (4,500 rcf) for 1 minute and freeze-dried overnight.

Results

Microparticles were made of PLGA copolymers of different L:G ratios and solvents using the S/O/W emulsion method. The efficacy of loading of botulinum toxin into the different microparticles is demonstrated in Table 8. The Samples #1 and #2 in Table 8 were made to study the solvent effect, and samples #2 and #3 having toxin were made to study effect of PLGA L:G ratio. Microparticles made of PLGA 75:25 had the protein loading efficiency of about 98% and PLGA 85:15 about 94%. The results indicate the S/O/W emulsion with the solvent-washed toxin provides stable conditions to make high productivity and reproducibility (see Table 8).

TABLE 8

Protein loading and loading efficiency of solvent-washed toxin/albumin loaded microparticles.

| # |  | Theoretical loading (%) | Protein loading (%) | Loading efficiency (%) |
|---|---|---|---|---|
| 1 | Albumin-PLGA (75:25 103,000 Da, DCM) | 6.25 | 6.12 | 97.9 |
| 2 | Toxin/albumin-PLGA (75:25 103,000 Da, DCM:Dx = 1:1) | 6.25 | 6.13 | 98.1 |
| 3 | Toxin/albumin-PLGA (85:15 102,000 Da, DCM:Dx = 1:1) | 6.25 | 5.86 | 93.7 |

The protein release from microparticles, as measured by albumin release, was governed by the solvent composition and L:G ratio. In this particular formulation study, the protein release was a function of the L:G ratio. The initial burst release decreased as the L:G ratio increased. In addition, the release rate was dependent on the solvent used for making microparticles.

Example 9: Activity of Toxin Released from Microparticles Made by Emulsion Method Methods Zn-precipitated toxin/albumin was prepared and divided into aliquots. Some samples were stored in a refrigerator as a control and other samples were washed with organic solvents for solvent washing. All samples were mixed into solution containing 500 µL of 100 mM EDTA while vortexing to dissolve the toxin/albumin precipitate. The dissolved toxin/albumin precipitate was transferred to an Amicon ultra-0.5 centrifugal filter device (Millipore, MW cut off 10,000 Da). The filter device was centrifuged for 3 minutes at 13,000 rcf. After removing the filtrate, pure water was added to the filter device up to 500 μL and centrifuged to remove EDTA and zinc chloride. After removing filtrate, 50 mM Tris pH 7.5 was added to the filter device up to 500 μL and centrifuged twice. The buffer-exchanged toxin/albumin was recovered by placing the filter device upside down in a clean microtube. The filter device was placed in the centrifuge and centrifuged for 3 minutes at 13,000 rcf. The toxin/albumin was collected into the clean microtube. Samples were tested for enzymatic activity using a FRET assay (BoTest kit from BioSentinel, Inc.).

The solvent-washed toxin was used to make PLGA microparticles by emulsion method. The microparticles were suspended in 5 mL of PBS-Tween (0.05%) (pH 7.5) containing 0.1% sodium azide at 37° C. in a shaking incubator at 50 rpm. At predetermined time points, each test tube was centrifuged at 5,000 rpm for 1 minute, and 500 μL of supernatant was withdrawn for the albumin release assay with the microBCA protein assay kit, for the botulinum toxin ELISA assay with the Tetracore BTX assay kit, and for the toxin enzymatic activity assay with the FRET assay kit according to standard operating procedure from the suppliers. After sampling, the test tubes were returned to the shaking incubator.

Results

Microparticles of PLGA 85:15 formulated using the emulsion method were used for FRET analyses to detect the toxin enzyme activity at the toxin concentration of 1-100 ng/mL.

The results of the FRET assay, along with ELISA assay, are provided in Table 9. The results established that the amounts of released toxin measured by ELISA are similar to those by the FRET assay, and the toxin released from the microparticles was enzymatically active. The FRET assay provided an easy and fast means of measuring the enzymatic activity of toxin without mouse paralysis experiments. The data indicated that the amount of toxin measured by the FRET assay is larger than the amount estimated from the ratio of toxin:albumin from the total albumin measurement (see Table 8). This suggests that most of the toxin in the solution was precipitated by zinc chloride and that toxin activity was not diminished throughout the microparticle manufacturing process.

TABLE 9

The enzymatic activity of solvent-washed toxin after released from microparticles at Day 1.

| Formulation | Protein assay (Total protein in the release medium) | ELISA assay (Total toxin in the release medium) | FRET assay (Total toxin in the release medium) |
|---|---|---|---|
| PLGA 85:15 (102k Da, DCM:Dx = 1:1) (5.9% protein loading) | Albumin 22% (314 μg), toxin (12 ng) | Toxin (13.3 ng) | Toxin (17.1 ng) |
| PLGA 85:15 (102k Da, DCM:Dx = 1:1) (6.0% protein loading) | Albumin 30% (560 μg), toxin (22 ng) | Toxin (22.0 ng) | Toxin (17.2 ng) |
| PLGA 75:25 (104k Da, DCM:Dx = 1:1) (6.1% protein loading) | Albumin 60% (833 μg), toxin (33 ng) | Toxin (32.2 ng) | Toxin (19.3 ng) |

Example 10: Microparticles Encapsulated in Crosslinked Hyaluronic Acid Gel

Method

A sample of HA crosslinked gel which encapsulated microparticles was prepared by dissolving 1% FITC-labelled hyaluronic acid (FITC-HA) in 0.01M $NaHPO_4$ buffer using an overhead stirrer. The microparticles were dispersed in 0.5 mL of HA solution in a 2 mL vial using a microtube thermal shaker at 40° C., 1000 rpm. Next the crosslinking agent, 1,2,7,8-diepoxyoctane (ODDE), was dissolved 10% v/v in water with shaking to disperse and 19 μL of the 10% ODDE were added to the microparticles/HA mixture while shaking. The solution was allowed to react at 40° C. with shaking 2.5 hours and was then stored at 4° C. overnight. This slurry was then pushed through a steel 600 μm (#30 mesh) sieve to break up HA and placed back into a 2 mL vial with a puncture cap. This was then vacuum dried for 2-3 days in a deep vacuum. This slurry was then redissolved in water to reconstitute and imaged under a fluorescence microscope.

Results

The formed FITC-HA gel was observed to encapsulate around the exterior of PLGA microparticles and it's location confirmed using fluorescence imaging of the FITC tag. The HA gel can is used to encapsulate not only PLGA microparticles but also precipitated botulinum toxin particles to aid in extending and controlling the botulinum toxin release rate.

Unless defined otherwise, all technical and scientific terms used herein have the same meanings as commonly understood by one of skill in the art to which the disclosed embodiments belong. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of formulating polymer particles for the controlled release of one or more encapsulated botulinum toxin proteins, comprising the steps of:
    (a) dissolving the botulinum toxin protein with a protein bulking agent in an aqueous solution to form a protein solution;
    (b) precipitating the protein from the protein solution with a precipitating agent selected from the group consisting of L-histidine methyl ester, L-cysteine ethyl ester, Nα-(tert-butoxycarbonyl)-L-asparagine, L-proline benzyl ester, N-acetyl-L-tryptophan, gentisic acid, pentetic acid, octanoic acid, zinc chloride, and combinations thereof to form a protein precipitate;
    (c) washing the protein precipitate one or more times with a wash solvent to form a solvent-washed protein precipitate, wherein the wash solvent is a solvent which retains the toxicity of the botulinum toxin in a mouse lethality test at 48 hours at a dose of 10 units/injection and is selected from the group consisting of acetone, acetonitrile, dioxane, ethanol, 2-methoxy ethyl acetate, methoxy ethanol, ethoxy ethanol, butoxy ethanol, 2-propanol, propylene glycol methyl ether, ethanediol, 1,2-propanediol, tert-butyl alcohol, diethylene glycol, and combinations thereof;
    (d) mixing or dispersing the solvent-washed protein precipitate in a solution containing a polymer to form a polymer-protein dispersion; and (e) forming polymer particles having uniformly dispersed therein between about 100 units and about 50,000 units of botulinum toxin protein and bulking agent complexed together with the precipitating agent, wherein the particles release an effective amount of botulinum toxin over a period of weeks.

2. The method of claim 1, wherein the precipitating agent in step (b) is zinc chloride.

3. The method of claim 2, wherein the concentration of the zinc chloride in the protein solution is 1% (w/v).

4. The method of claim 1, wherein the wash solvent in step (c) is selected from the group consisting of acetone, acetonitrile, dioxane, ethanol, and combinations thereof.

5. The method of claim 1, wherein the polymer solution in step (d) comprises a solvent selected from the group consisting of benzyl alcohol, n-butyl acetate, chlorobenzene, chloroform, dioxane, dichloromethane, ethyl acetate, ethyl benzoate, ethyl formate, methyl formate, methyl n-propyl ketone, phenethylamine, triacetin, trichloroethylene, and combinations thereof.

6. The method of claim 5 wherein the solvent is a combination of dioxane and dichloromethane or a combination of ethyl acetate and dichloromethane.

7. The method of claim 1 wherein the polymer-protein dispersion is formed into particles using a micropatterned template.

8. The method of claim 7 wherein the micropatterned template comprises poly(vinyl alcohol).

9. The method of claim 1 wherein the particles are formed from an emulsion formed by emulsifying the polymer-protein dispersion with a non-solvent of the polymer.

10. The method of claim 9 wherein the non-solvent is an aqueous non-solvent pre-conditioned with an organic solvent or mixture of organic solvents that dissolve the polymer.

11. The method of claim 10 wherein the organic solvent used for preconditioning is dichloromethane.

12. The method of claim 11 wherein the emulsion comprises dichloromethane in a concentration between 0.1% and 1.3% in an aqueous solution.

13. The method of claim 10 wherein the organic solvent used for preconditioning is ethyl acetate.

14. The method of claim 9 wherein the emulsion comprises ethyl acetate in a concentration between 0.1% and 8.7% in aqueous solution.

15. The method of claim 9 wherein the emulsion is mixed with an overhead stirrer or a homogenizer.

16. The method of claim 9 wherein the emulsion is an aqueous emulsion containing a dissolution prevention agent selected from the group consisting of L-histidine methyl ester, L-cysteine ethyl ester, Nα-(tert-butoxycarbonyl)-L-asparagine, L-proline benzyl ester, N-acetyl-L-tryptophan, gentisic acid, pentetic acid, octanoic acid, and zinc chloride.

17. The method of claim 16 wherein the dissolution prevention agent is zinc chloride.

18. The method of claim 17 wherein the concentration of zinc chloride in the emulsion is between 0.1% and 10% w/v.

19. The method of claim 1 wherein the botulinum toxin is selected from the group consisting of botulinum toxin types A, B, C, D, E, F, G, and mixtures thereof.

20. The method of claim 19, wherein the botulinum toxin is a botulinum toxin type A.

21. The method of claim 1, wherein the polymer particles have dispersed therein between about 100 units and about 30,000 units of botulinum toxin A and bulking agent complexed together with the precipitating agent.

22. The method of claim 1, wherein the polymer particles have dispersed therein between about 100 units and about 30,000 units of botulinum toxin B and bulking agent complexed together with the precipitating agent.

23. The method of claim 1, wherein the protein bulking agent comprises a serum albumin protein.

24. The method of claim 1, wherein the polymer is a biodegradable polymer.

25. The method of claim 24, wherein the biodegradable polymer is selected from the group consisting of polylactide, poly(lactide-co-glycolide), polycaprolactone, polyorthoester, poly(ester amide), polyanhydride, poly(p-dioxanone), poly(alkylene oxalate), poly(lactide-co-glycolide)-poly(ethylene glycol) block copolymers, collagen, proteins, hyaluronic acid, polysaccharides, nucleic acids, and blends and copolymers thereof.

26. The method of claim 5 wherein the biodegradable polymer is a poly(lactide-co-glycolide) having the lactide:glycolide (L:G) ratio of between about 50:50 and 100:1, inclusive.

27. The method of claim 6 wherein the biodegradable polymer is a poly(lactide-co-glycolide) having the lactide:glycolide (L:G) ratio of between about 75:25 and 85:15, inclusive.

28. The method of claim 1, wherein the solvent-washed protein precipitate is dried by freeze-drying.

29. The method of claim 1, wherein the solvent-washed protein precipitate is directly mixed with the polymer solution.

30. The method of claim 1, further comprising reducing the size of the solvent-washed protein precipitate by dry or wet milling.

31. The method of claim 30, wherein the milling temperature is controlled with solidified carbon dioxide or liquid nitrogen.

32. The method of claim 30, wherein the size of the solvent-washed protein precipitate is reduced by wet milling with n-butyl acetate, dioxane, dichloromethane, ethyl acetate, or combinations thereof.

33. A pharmaceutical composition, comprising a plurality of polymer particles having uniformly dispersed therein between about 100 units and about 50,000 units of botulinum toxin complexed with a protein bulking agent and precipitated by a precipitating agent selected from the group consisting of L-histidine methyl ester, L-cysteine ethyl ester, Nα-(tert-butoxycarbonyl)-L-asparagine, L-proline benzyl ester, N-acetyl-L-tryptophan, gentisic acid, pentetic acid, octanoic acid, zinc chloride, and combinations thereof,
 wherein the precipitated botulinum toxin complexed with the protein bulking agent is washed with a wash solvent prior to encapsulation, wherein the wash solvent retains the toxicity of the botulinum toxin in a mouse lethality test at 48 hours at a dose of 10 units/injection and is selected from the group consisting of acetone, acetonitrile, dioxane, ethanol, 2-methoxy ethyl acetate, methoxy ethanol, ethoxy ethanol, butoxy ethanol, 2-propanol, propylene glycol methyl ether, ethanediol, 1,2-propanediol, tert-butyl alcohol, diethylene glycol, and combinations thereof,
 and wherein the botulinum toxin is released in an effective amount over a period of weeks.

34. The pharmaceutical composition of claim 33, wherein the polymer particles are dispersed in a diluent consisting of an aqueous thermosensitive polymer solution.

35. The pharmaceutical composition of claim 34 wherein the aqueous thermosensitive polymer solution transitions between liquid and gel within the range of 4° C. to 40° C.

36. The pharmaceutical composition of claim 35 wherein the aqueous thermosensitive polymer solution transitions between liquid and gel within the range of 20° C. to 38° C.

37. The pharmaceutical composition of claim 34 wherein the aqueous thermosensitive polymer is selected from poly (lactide-co-glycolide)-b-poly(ethylene glycol)-b-poly(lactide-co-glycolide), poly(lactide)-b-poly(ethylene glycol)-b-poly(lactide), poly(lactide-co-caprolactone)-b-poly(ethylene glycol)-b-poly(lactide-co-caprolactone), poly(caprolactone)-b-poly(ethylene glycol)-b-poly(caprolactone), methoxy poly(ethylene glycol)-b-poly(caprolactone), or combinations thereof.

38. The pharmaceutical composition of claim 34 wherein the aqueous thermosensitive polymer solution contains the thermosensitive polymer at a concentration between 5% and 40% (w/v).

39. The pharmaceutical composition of claim 34 wherein the aqueous thermosensitive polymer solution contains the thermosensitive polymer at a concentration between 10% and 30% (w/v).

40. The pharmaceutical composition of claim 33, wherein the polymer particles are dispersed in a diluent consisting of a gel-forming solution or a gel.

41. The pharmaceutical composition of claim 40 wherein the gel-forming solution is hyaluronic acid and the gel is crosslinked hyaluronic acid.

42. The pharmaceutical composition of claim 33, wherein the botulinum toxin is selected from the group consisting of botulinum toxin types A, B, C, D, E, F, G, and mixtures thereof.

43. The pharmaceutical composition of claim 33 further comprising one or more therapeutic, prophylactic, or diagnostic agents.

44. The pharmaceutical composition of claim 34, wherein the polymer particles are formulated according the steps of:
 (a) dissolving the botulinum toxin protein and a bulking agent selected from the group consisting of albumin, gelatin, and transferrin, in an aqueous solution to form a protein solution;
 (b) precipitating the botulinum toxin protein and the bulking protein complexed together from the protein solution using a precipitating agent selected from the group consisting of L-histidine methyl ester, L-cysteine ethyl ester, Nα-(tert-butoxycarbonyl)-L-asparagine, L-proline benzyl ester, N-acetyl-L-tryptophan, gentisic acid, pentetic acid, octanoic acid, zinc chloride, and combinations thereof to form a protein precipitate;
 (c) washing the protein precipitate one or more times with a wash solvent to form a solvent-washed protein precipitate, wherein the wash solvent is a solvent which retains the toxicity of the botulinum toxin in a mouse lethality test at 48 hours at a dose of 10 units/injection and is selected from the group consisting of acetone, acetonitrile, dioxane, ethanol, 2-methoxy ethyl acetate, methoxy ethanol, ethoxy ethanol, butoxy ethanol, 2-propanol, propylene glycol methyl ether, ethanediol, 1,2-propanediol, tert-butyl alcohol, diethylene glycol, and combinations thereof;
 (d) mixing or dispersing the solvent-washed protein precipitate in a solution containing a polymer to form a polymer-protein dispersion; and
 (e) forming polymer particles encapsulating the solvent-washed protein precipitate from the polymer-protein dispersion.

45. A pharmaceutical composition, comprising a plurality of polymer particles having uniformly dispersed therein botulinum toxin complexed with albumin and precipitated by a precipitating agent, which releases an effective amount of botulinum toxin over a period of weeks, formulated according to the steps of:
 (a) dissolving the botulinum toxin and albumin proteins in an aqueous solution to form a protein solution;
 (b) precipitating the protein from the protein solution with a precipitating agent selected from the group consisting of L-histidine methyl ester, L-cysteine ethyl ester, Nα-(tert-butoxycarbonyl)-L-asparagine, L-proline benzyl ester, N-acetyl-L-tryptophan, gentisic acid, pentetic acid, octanoic acid, zinc chloride, and combinations thereof to form a protein precipitate;
 (c) washing the protein precipitate one or more times with a wash solvent to form a solvent-washed protein precipitate, wherein the wash solvent is a solvent which retains the toxicity of the botulinum toxin in a mouse lethality test at 48 hours at a dose of 10 units/injection and is selected from the group consisting of acetone, acetonitrile, dioxane, ethanol, 2-methoxy ethyl acetate, methoxy ethanol, ethoxy ethanol, butoxy ethanol, 2-propanol, propylene glycol methyl ether, ethanediol, 1,2-propanediol, tert-butyl alcohol, diethylene glycol, and combinations thereof;
 (d) mixing or dispersing the solvent-washed protein precipitate in a solution containing a polymer to form a polymer-protein dispersion; and
 (e) forming from the polymer-protein dispersion, polymer particles having uniformly distributed therein between about 100 units and about 50,000 units of botulinum toxin complexed with the albumin and precipitated by the precipitating agent.

46. The pharmaceutical composition of claim 45, wherein the polymer particles are dispersed in a diluent consisting of an aqueous thermosensitive polymer solution.

47. The pharmaceutical composition of claim 45, wherein the polymer particles are dispersed in a diluent consisting of an aqueous gel.

* * * * *